United States Patent
Coffino et al.

(12)

(10) Patent No.: US 6,217,864 B1
(45) Date of Patent: *Apr. 17, 2001

(54) METHOD FOR TARGETED DEGRADATION OF INTRACELLULAR PROTEINS IN VIVO OR EX VIVO

(75) Inventors: Philip Coffino, San Francisco; Xianqiang Li, Palo Alto, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/243,273

(22) Filed: Feb. 2, 1999

Related U.S. Application Data

(63) Continuation-in-part of application No. 08/603,575, filed on Feb. 23, 1996, now Pat. No. 5,866,121.
(51) Int. Cl.[7] .......................... A61K 38/48; A61K 38/51; G01N 33/55; C12P 21/06
(52) U.S. Cl. .................. 424/94.63; 424/94.5; 424/185.1; 424/192.1; 435/7.6; 435/69.1; 530/350
(58) Field of Search ................................ 424/94.63, 94.5, 424/185.1, 192.1; 435/7.6, 69.1; 530/350

(56) References Cited

U.S. PATENT DOCUMENTS 5,866,121 * 2/1999 Coffino et al. ..................... 424/94.63

OTHER PUBLICATIONS

Li et al. Molecular and Cellular Biology, Jan. 1994, 14(1) : 87–92.*
Goltzer et al. Nature 349:132–138 (1991).*
Crook et al. Cell 67:547–556 (1991).*
Elias et al. Eur. J. Biochem. (Apr. 1, 1995), vol. 229, No. 1, pp. 276–283.*

* cited by examiner

*Primary Examiner*—Ponnathapu Achutamurthy
*Assistant Examiner*—Tekchand Saidha
(74) *Attorney, Agent, or Firm*—Hana Verny

(57) ABSTRACT

A method for in vivo selective targeted degradation of intracellular proteins in situ by inducing in vivo or ex vivo in cells a production of dual-function protein comprising N-terminal domain as well as a C-terminal domain or delivering the dual-function protein. The N-terminal domain of the dual-function protein destabilizes the target protein and directs its degradation when linked to it through a linker between the target protein and between the protein agent of the invention. The protein degradation directing N-terminal domain is a subregion within the first 97 amino acids corresponding to the N-terminus of protein antizyme.

17 Claims, 9 Drawing Sheets

FIG. 1A
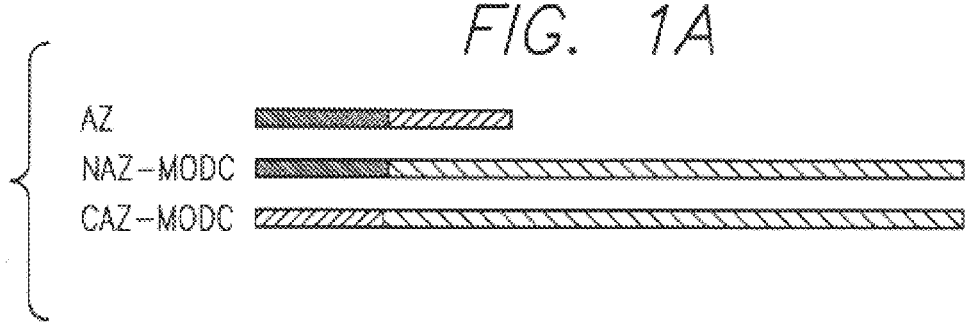
FIG. 1B
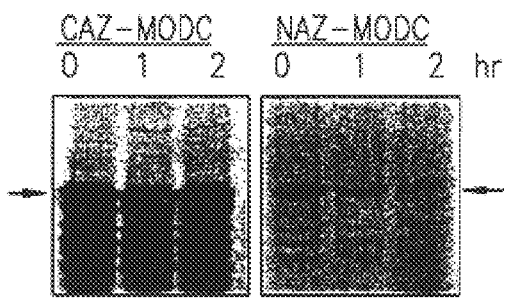
FIG. 2A
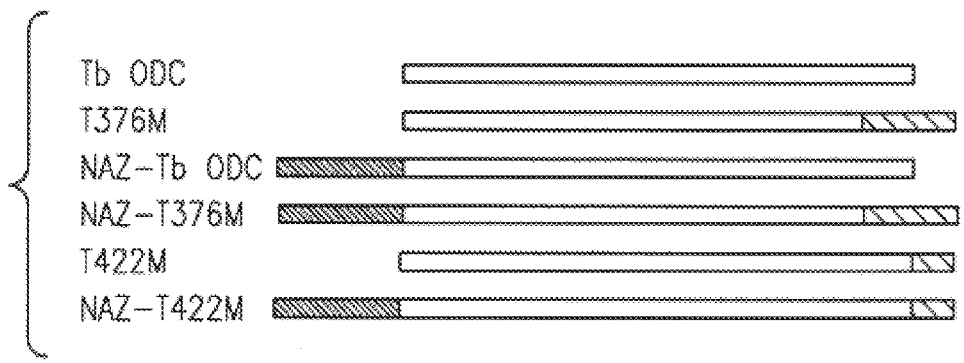
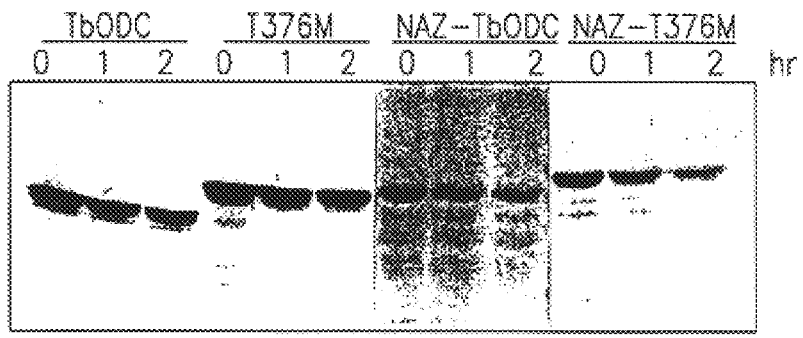
FIG. 2B

FIG. 2C
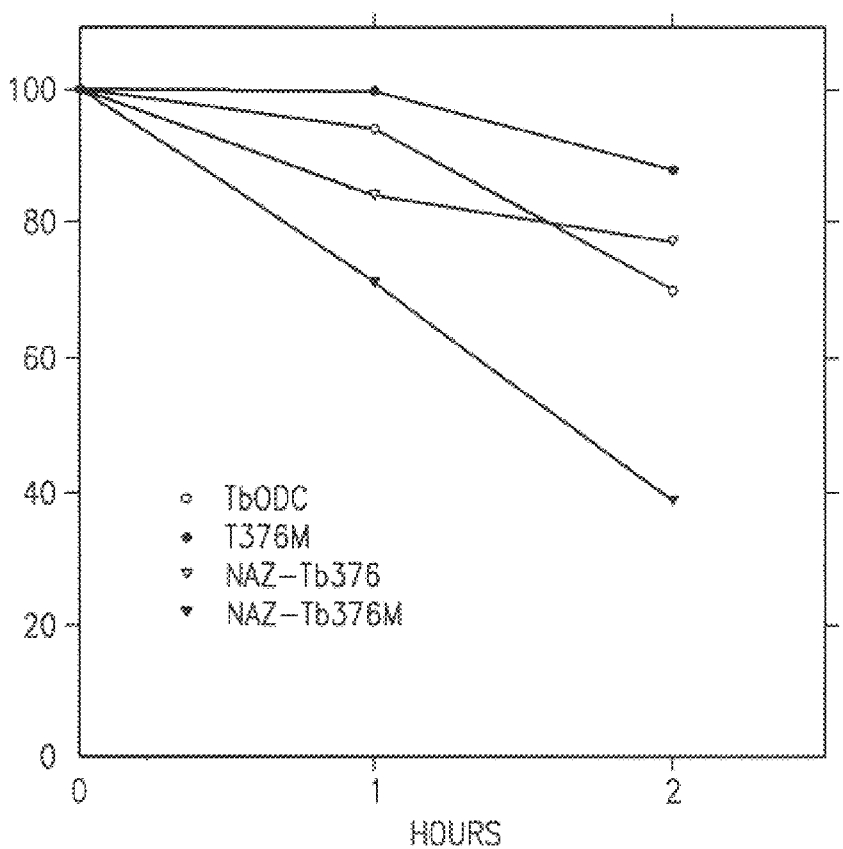
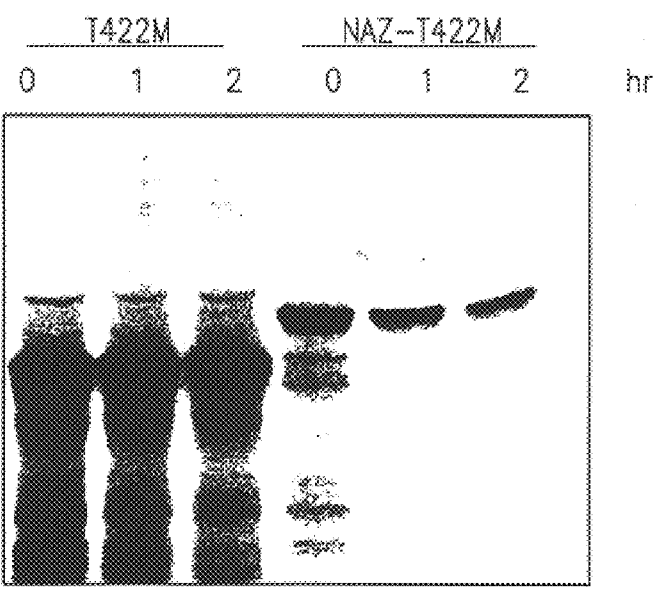
FIG. 2D

FIG. 5A
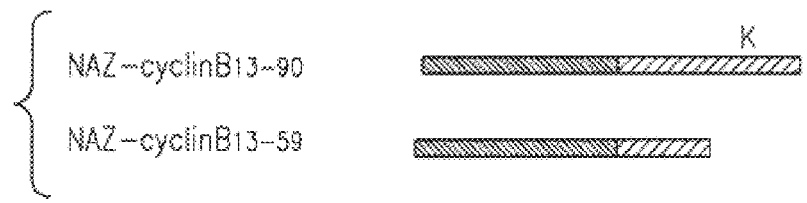
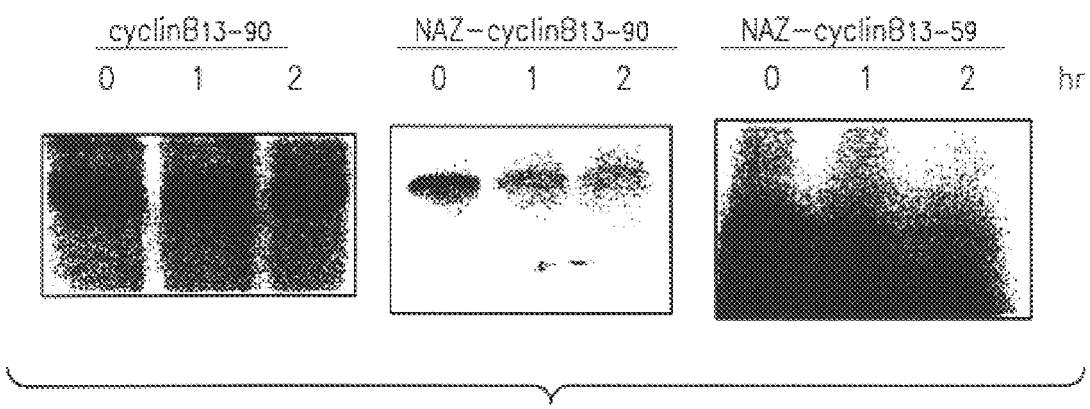
FIG. 5B
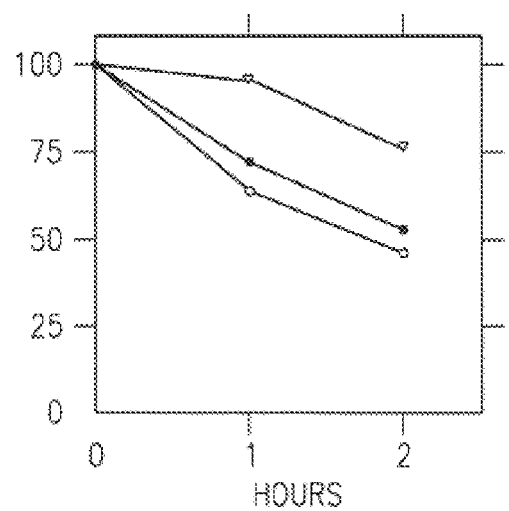
FIG. 5C

METHOD FOR TARGETED DEGRADATION OF INTRACELLULAR PROTEINS IN VIVO OR EX VIVO

This is a continuation-in-part application of U.S. application Ser. No. 08/603,575, filed Feb. 23, 1996 issued as U.S. Pat. No. 5,866,121 on Feb. 2, 1999.

This invention was developed partially with NIH grants GM45335 and RO1-CA29048. Government may have certain rights to this invention.

BACKGROUND OF THE INVENTION

1. Field of Invention

The current invention concerns a method for in vivo or ex vivo targeted degradation of intracellular proteins in situ. In particular, the invention concerns the method for degradation of intracellular proteins by inducing in cells the production of a dual-function protein containing a domain that directs a selective degradation of targeted proteins to which it is attached as well as a domain that acts as a linker between the dual-function protein and the target protein. The protein degradation directing domain is a subregion within 97 amino acids which corresponds to the N-terminus of protein antizyme (NAZ). The invention further concerns a method for inducing in vivo or ex vivo in cells the production of the dual-function protein consisting of NAZ and linker directed to destruction of specific cellular target proteins.

2. Background and the Related Art

The body produces a large number of proteins which direct and regulate numerous physiological functions. The rapid turnover of these proteins is important in regulating cell growth and metabolism. These proteins are, under normal circumstances, strictly regulated by physiological feedback, which assures that when the level of certain protein in the body reaches desired level, a regulatory mechanism normally present in the body takes over the control of that particular protein production and either decreases it to the level which is sufficient for a normal physiological function of that protein or temporarily terminates its production.

In many instances, however, due to some pathological or pathophysiological conditions, such endogenous control is disturbed and overproduction or underproduction of certain proteins occurs.

Underproduction of these proteins is typically corrected by providing substitute proteins or drugs which would stimulate the protein production.

In case of overproduction of certain proteins, such as, for example, hormones, the problem is much more serious and typically can be corrected only by inhibiting the production of these proteins by drugs or synthetic enzymatic inhibitors. Very often these drugs are not overly selective for the particular protein but will also affect, that is inhibit, the production of other proteins. Additionally, when administered systemically, these inhibitors have often undesirable secondary systemic symptoms.

It would be, therefore, advantageous to have available a method for in vivo or ex vivo induction of selective destruction of targeted proteins in situ.

Proteins that turn over rapidly in the body are of special interest because they can quickly adjust their abundance in response to changes in synthesis or degradation. Some labile proteins have been found to interact with a second protein that promotes their degradation. Examples of these proteins are lysosome-degraded proteins which interact with 70-kD heat shock protein and tumor suppressor p53 which interacts with viral oncoproteins (*Science*, 346:382–385 (1989) and *Cell*, 67:547–556 (1991)).

Several methods are presently under consideration as modifiers of protein degradation. The first approach uses inhibitors of the proteasome or other viral or cellular proteases. These methods lack substrate specificity and in general modify the action of the proteolytic machinery rather than its action on specific substrates.

The second approach utilizes ubiquitination. Ubiquitination is a natural process introducing a modification consisting of the attachment of multiple copies of the protein ubiquitin that triggers proteolysis of many short-lived proteins (*Nature*, 357: 375–379 (1992); *Microbiol. Rev.*, 56: 592–621 (1992); *Ann. Rev. Biochem.*, 61: 761–807 (1992); *J. Biol. Chem.*, 268: 6065–6068 (1993).

Attempts were made previously to provide a method for specific proteolytic removal of proteins via the ubiquitin-dependent proteolytic pathway. This method is, however, complicated, laborious and not suitable for clinical use. Degradation via the ubiquitin pathway requires the prior attachment of multiple ubiquitins to the target proteins. This attachment is accomplished by a family of enzymes designated ubiquitin-conjugating enzymes (E2), some of which use domains near their C-termini for target recognition. For example, *PNAS*, 92: 9117–9121 (1995) describes a method for modified ubiquitination by generating chimeric ubiquitin-conjugating enzymes that recognize and ubiquitinate their binding partners with high specificity in vitro. This method comprises forming a fusion containing a linker and one of the enzymes that participates in ubiquitination, thus ubiquitinating specific proteins and targeting them for destruction.

The method described in *PNAS*, above, however, depends on fusion maintaining enzymatic activity of E2 in general and particularly for the intended target. Multiple ubiquitins must be transferred to a substrate to cause its degradation and additional enzymes collectively called E3 may be needed for substrate ubiquitination. So far, this method has only been tested in vitro and its effectiveness and substrate specificity in vivo have not been demonstrated.

The selective targeted protein degradation method alternative to ubiquitination has not been previously described but would be very useful in controlling excess production and/or inhibition of production of certain proteins or their end-product compounds by way of selective degradation of targeted proteins. Such degradation in vivo would be useful in controlling diseases caused by the overproduction of certain proteins or compounds. Examples of such diseases are hormonal disorders, carcinogenic growth, viral, bacterial or parasitic infections, etc.

It would therefore, be advantageous to provide a method for in vivo or ex vivo substrate specific and targeted degradation of proteins in situ which method would be effective in vivo, in which the need for ubiquitination would be eliminated and the whole degradation process would be simplified by attaching a protein element that provides a functional alternative to ubiquitination to target proteins.

Physiological feedback control over protein production or termination of such production has been known and studied, for example, on polyamine biosynthetic enzymes. Polyamines presence in the body is essential for cell growth and proliferation. The key enzyme in the biosynthesis of the polyamines, ornithine decarboxylase (ODC), is highly regulated. Mammalian ODC is also one of the group of the most short lived of proteins. Its turnover can proceed along two different metabolic pathways: constitutive pathway and polyamine dependent pathway. The activity of the ODC enzyme is increased by cell growth in cancer but is decreased by the presence of an excess of polyamines. However, polyamine-promoted degradation of ODC seems to involve another protein.

Feedback regulation of the ODC enzyme by polyamines occurs via induction of a protein called antizyme. (*Biochem. Biophys. Acta,* 428: 456–465 (1976); *PNAS,* 73:1858–1862 (1976); *J. Biol. Chem.,* 259:10036–10040 (1984); *J. Biochem.,* 108:365–371 (1990) and *Gene,* 113:191–197 (1992)).

In their previous research, inventors discovered that regulated degradation of ODC requires interaction of two ODC regions with a specific polyamine-inducible protein antizyme. These regions are located near C-terminus and near N-terminus of ODC. This specific polyamine-inducible antizyme was found to bind to ODC, inhibit its activity and accelerate its degradation. The antizyme-ODC binding seems to be required for regulated degradation of ODC (*Mol. Cell. Biol.,* 12: 3556–3562 (1992)). The interaction of the ODC antizyme with a ODC binding element located near the N-terminus of ODC was found essential but not sufficient for regulation of the enzyme by polyamines. The second ODC element present at the C-terminus of ODC is required for the degradation process. Thus, both the C-terminal degradation region and a binding element near the N-terminus of ODC are required for the degradation process of ODC (*Mol. Cell. Biol.,* 13: 2377–2383 (1993)).

In the studies described in (*Mol. Cell. Biol.,* 14: 87–92 (1994) selective degradation of ODC was found to be mediated by antizyme which binds to a region near the ODC N-terminus. This interaction induces a conformational change in ODC that exposes its C-terminus and inactivates the ODC. Additionally, it was found that while the C-terminal half of antizyme alone can bind to and inactivate ODC and alter its conformation, it cannot direct degradation of the enzyme either in vitro or in vivo. A portion of the N-terminal half of antizyme must be present to promote such degradation.

While the above findings concerning the degradation of ODC are scientifically interesting, they are without practical utility. The ODC is closely regulated and as a short life enzyme, it is quickly disposed of. Other than scientific importance and the invention background, the findings described above do not provide a method or means for selective and targeted degradation of proteins intracellularly which would have general utility.

It is, therefore, a primary objective of this invention to provide a method and means for selective and targeted degradation of proteins in situ by administering to a subject in need thereof a dual-function protein produced ex vivo, or by inducing in vivo in the subject in need of such treatment, the endogenous production of an effective amount of dual-function protein comprising a linker domain for specific binding to a target protein as well as a N-terminus domain of antizyme capable, when complexed with the target protein via the linker, of destabilizing it and changing it in such a way that it becomes labile and subject to destruction.

All patents, patent application and publication cited herein are hereby incorporated by reference.

SUMMARY

One aspect of the current invention is a method for selective and targeted degradation of proteins in vivo.

Another aspect of the current invention is a method for selective and targeted degradation of endogenously present proteins by generating dual-function proteins comprising two distinct functional domains able to form a complex with the target protein and cause its degradation.

Another aspect of the current invention is a method and means for selective and targeted degradation of proteins in situ by administering to a subject in need thereof a dual-function protein generated ex vivo or by inducing in vivo in the subject in need of such treatment the endogenous production of an effective amount of a dual-function protein comprising a linker domain capable of complexing with the target protein, and a N-terminus of antizyme capable of destabilizing the target protein in such a way that it becomes labile and subject to degradation.

Still another aspect of the current invention is a method for degradation of intracellular proteins by inducing in cells the production of a subregion of about 97 amino acids which corresponds to the N-terminus domain of protein antizyme (NAZ) that directs the degradation of proteins to which it attaches, wherein said NAZ domain is able to be attached to the target protein and direct its degradation.

Still another aspect of the current invention is a method for inducing in cells the production of NAZ domain in a form directed to destruction of specific cellular target proteins via its association with a target specific linker.

Still yet another aspect of the current invention is a method for in vivo treatment of hormonal diseases, metabolic disorders, tumorigenic diseases, viral infections, bacterial infections or parasitic infection.

BRIEF DESCRIPTION OF DRAWINGS

FIG. 1 illustrates in vitro degradation of mouse ODC (MODC) induced by fusion of ODC to N-terminus of antizyme (NAZ).

FIG. 2 illustrates TbODC degradation induced by the N-terminus of antizyme (NAZ) and C-terminus of mouse ODC.

FIG. 5 illustrates NAZ-induced degradation of cyclin B 13–90 (with ubiquitination site) and cyclin B 13–59 (without ubiquitination site).

DEFINITIONS

Figure 3A:
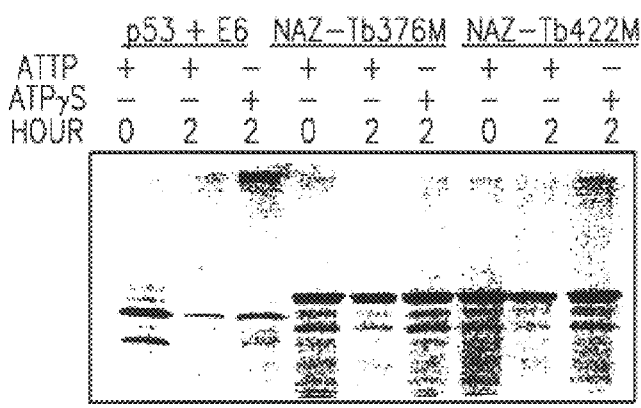
FIG. 3 illustrates effect of ATP-γ-S on degradation of NAZ-Tb376M and NAZ-Tb422M.

As used herein:

"Dual-function protein" means a protein containing a domain controlling binding and a domain directing protein destabilization and degradation.

"Antizyme" or "AZ" means a reversible, tightly binding polyamine-induced protein inhibitor of ornithine decarboxylase activity.

"Linker" or "link" means a protein or peptide capable of recognizing, identifying and binding to a target protein or peptide. It also means a binding domain present within a dual-function protein typically near its C-terminus, wherein said protein additionally contains the second NAZ domain located near the protein N-terminus. A primary function of the linker is to bind to and in this way to deliver NAZ domain to a target protein.

"ODC" means ornithine decarboxylase.

"NAZ" means N-terminus of antizyme or other protein which represents a domain, i.e. defined portion of approximately 97 amino acids in size, which domain carries a critical signal that acts as a functional module which when attached to heterologous proteins causes those proteins to be rapidly degraded.

"CAZ" means C-terminal half of antizyme.

"GST" means glutathione S-transferase.

"Target protein" means any protein able to be connected to NAZ or containing a degradation region required for cooperation with the NAZ domain. The target protein includes all proteins which are per se already more or less unstable, in that they contain a degradation domain. This includes substantially all proteins important for cellular regulation. These proteins are, under appropriate cellular conditions, subject to rapid intracellular degradation by way of feedback and thus contain a degradation domain. Additionally, target proteins are also other normally stable proteins where the degradation region could be induced or could be incorporated into NAZ-linker protein.

"Covalent association" means association of two protein regions present within one protein chain.

"Non-covalent association" means association of two protein regions present within two separate protein chains.

"In vivo" means in the living body and refers to chemical reactions occurring within cells or body fluids or tissues.

"Ex vivo" means and refers to chemical reactions performed outside of the living body, typically in the living cells.

DETAILED DESCRIPTION OF THE INVENTION

This invention concerns a method for an in vivo or ex vivo degradation of intracellular proteins in situ. The method achieves the substrate specific targeted degradation of intracellular proteins by providing to a subject in need of such treatment a dual-function protein generated ex vivo or by inducing intracellularly the production of a dual-function protein. The dual-function protein contains two domains wherein one domain is a subregion of about 97 amino acids defining the N-terminus of protein antizyme (NAZ) and a second domain is a linker. The NAZ domain directs the degradation of proteins to which it is attached by way of the linker. The second domain, the linker, binds to a target protein with high affinity and specificity.

I. A Method For Degradation of Target Cellular Proteins

This invention is based on finding that a naturally occurring protein called antizyme (AZ) can bind to a second naturally occurring protein and under conditions described herein, induce its degradation. The second protein, when associated with antizyme, is rapidly destroyed by enzyme proteasome, the major cellular protease. Antizyme is not itself destroyed.

The invention is further based on additional discovery that a defined portion of antizyme, approximately and up to about 97 amino acids in size, carries the critical signal that directs degradation of the second protein.

Furthermore, it has been now found that this domain, located near the antizyme N-terminus (NAZ), acts as a functional module for destruction of proteins to which it can be attached. When attached to other proteins by way of the linker, the NAZ domain causes those proteins to be rapidly degraded.

In its broadest form, the invention provides a method and a means for destroying specifically targeted cellular proteins in situ in in vivo conditions. The invention consists of several elements.

One of the elements of the invention is production or generation of a dual-function protein containing the NAZ domain and the linker domain, wherein the linker domain is able to selectively bind to a target protein, thus delivering NAZ domain to the target protein. Through its binding to the target protein, the NAZ domain provides a signal for the target protein destruction.

The second element of the invention is a delivery of said dual-function protein to a subject in need thereof. The delivery of the dual-function protein to the subject comprises inducing production of a compound comprising NAZ-linker domains within the subject's cells in vivo, production of a protein expressed from a specific subregion of the NAZ domain in vivo or ex vivo coding sequence by way of gene therapy, or producing said protein in ex vivo system and delivering the protein to a target region cells or tissue.

For any of the above mentioned routs of delivery, cells or organisms may be pretreated with polyamines or any other compound which causes production or synthesis of antizyme or a production of the protein functioning in substantially the same way as antizyme. NAZ and the linker act as specific seekers of target protein when delivered to cells.

The method is highly specific and efficient. The linker is selected to have appropriate substrate specificity. Consequently, the protein degradation is highly specific and discriminatory. Antizyme is normally not destroyed during the degradation of the target protein, and is therefore available to be reused. Therefore, one molecule of antizyme-linker protein is able to direct the destruction of many molecules of the target protein.

A. Dual-Function Protein

Dual-function protein comprises two functionally different domains, namely the degradative domain and connecting domain, namely liner or a ligand.

The degradative domain of the dual-function protein can be antizyme or any other protein which contains an amino acids region therein identified as NAZ domain or region similar to NAZ domain in its functionality. Functionality, in this respect, means that the alternative protein must have the ability to induce or to destroy the target protein in the same manner as antizyme. The alternative protein must also be able to form a dual-function protein with a suitable linker domain, which linker domain is able to identify and recognize the target protein and bind to its degradation region.

Antizyme in quantities necessary to achieve the target protein degradation can be intrinsically induced by administration of dietary or injectable polyamines. Polyamines are natural and safe constituents of all living organisms. They are products of the biosynthetic pathway initiated and controlled by ODC. Polyamines have been shown (*Cell*, 80: 51 (1995)) to induce a shift in the reading frame the antizyme mRNA needs for its translation into antizyme protein. Antizyme containing fusion proteins are therefore easily produced at will by treating the subject in vivo or cells ex vivo with readily available, safe and structurally simple polyamines or their analogs.

Tissue specific promoters for expression of the antizyme-linker mRNA with translation conditional on polyamine treatment are used for control of the time and site of protein degradation.

Methods used for production of antizyme cDNA, expression vectors, preparation of antizyme fusion proteins with linkers, transcription of the cDNA into RNA and translation into protein are described in Examples 1–3 and 5. Recombinant DNA constructs for expression of fusion proteins by in vitro transcription and translation, useful for ex vivo preparation of dual-function proteins or for in vivo gene therapy are described in Example 7. Complexing of antizyme with a linker domain and with the target protein is described in Example 9, and transfection and in vivo degradation assay is described in Example 11.

The degradative domain of the dual-function protein is selected from the group of proteins or peptides, with exclusion of ubiquitin, that function like antizyme. These proteins, like antizyme, upon association with the target protein cause such target protein to be destroyed by the proteasome.

The dual-function protein thus is any protein associated with a target specific linker or ligand which is functionally related to the antizyme whether or not such protein or peptide is structurally related to antizyme. The dual-function protein may act by causing the potential target to be brought to the proteasome or by activating the degradative activity of the proteasome or by any other means and mechanism.

B. NAZ Domain of the Dual-Function Protein

NAZ domain of the dual-function proteins comprises a defined portion comprising about 97 amino acids in the proximity of the amino N-terminus of the dual-function protein. NAZ domain is a region comprising amino acids 1–97 of the Z1 clone (*Gene*, 113: 191–197 (1992)). The NAZ domain function persist if amino acids 1–54 or amino acids 85–98 are removed from antizyme. Therefore, the required region of NAZ domain needed for degradative function is contained within amino acids 55–84. This region contains 30 amino acids.

The N-terminus domain promotes and directs degradation of heterologous proteins when attached to them. This domain is not necessary and not responsible for the interaction of the dual-function protein with the target protein but it is necessary to induce the target protein degradation. The NAZ domain destabilizes the target protein and confers on the target protein the liability which was not present before the NAZ domain association with the target protein. The NAZ domain thus readily induces degradation of unstable proteins but also induces degradation of proteins which are otherwise stable and which, without the NAZ domain attachment, would not be subject to degradation. NAZ domain presence drives proteins down a proteasome-mediated degradation pathway with downstream elements common both for non-ubiquitination and ubiquitination and therefore the need for ubiquitination can be bypassed and is eliminated by the method of the invention. It is one of the advantages of the current invention that the target protein degradation is achieved without ubiquitination.

NAZ domain has been shown to be effective in promoting in vitro liability and degradation. This in vitro liability can be conferred on natural substrates of in vivo degradation and used to promote the degradation in vivo.

The liability and degradation of proteins in vivo can be achieved in two ways. One way utilizes a gene therapy whereby the transcription and translation system for production of the specific dual-function protein is induced in the subject's own cells or preferably, the specific dual-function protein is produced ex vivo in subject's own cells or in vitro, as described below, and delivered to the subject using various delivery routes allowing a delivery to the target cells or tissue.

NAZ domain of antizyme has been previously shown to act within ornithine decarboxylase. However, the finding that the NAZ domain is able to act as a functional module on proteins not directly in the ODC metabolic pathway is unexpected and surprising and was until now never described, disclosed or even suspected to exist. It is surprising that a region of protein specific for destruction of ODC would also assert similar function on other unrelated proteins.

The dual functionality of ODC specific antizyme has not been previously known and its use for selective and targeted destruction of unrelated proteins in vitro and in vivo is a novel discovery.

C. A Linker Domain of the Dual-Function Protein

The linker domain of the dual-function protein is typically localized in the proximity of the C-terminus of the dual-function protein. This domain has a distinct and separate function in the target protein degradation according to the invention in that it recognizes and identifies the target protein, binds to it and in this way delivers NAZ domain to the target protein. The linker domain itself is not involved in the destruction of the target protein.

The linker is found or designed in several ways. Naturally occurring interaction partners of the target proteins may be already known. If known, the linker and the target protein are tested in vitro to find optional condition, i.e., affinity concentration needed for binding selection and particularly specificity of binding. The potential linker may otherwise be found by systemic screening, such as for example by the yeast two hybrid system, a yeast-based system for identifying and purifying proteins that bind to a protein of interest or by affinity chromatography methods well known in the art and used for such purposes. In alternative, monoclonal antibodies are made or other variants are employed such as, for example, phage peptide display libraries screening or chimeric drug ligands, all known in the art.

Candidates for linkers are identified as above according to the methods described in *Nucleic Acids Res.* 23:1152–6 (1995) for yeast two hybrid trap, in *Proc. National Acad. Sci. (USA)*, 92:11456–60, (1995) for natural partners, peptide library screening etc. Other techniques, such as chimeric drug ligands, according to *Science*, 262:1019 (1993) may be used to bind target to linker.

Effective linkers must have two properties, high affinity and high specificity. Affinity is normally described by its equilibrium constant, determinable by standard methods, such as, for example, equilibrium dialysis. Specificity refers to association with the intended target, to the relative exclusion of alternative unintended targets.

To determine whether candidate linkers are likely to be of adequate specificity, linkers are tested to see whether there are cellular proteins other than the intended target with which they associate. This is achieved, for example, by immobilizing the candidate linker on an affinity column matrix and by identifying proteins from cell extracts that associate with the column matrix to the exclusion of other cellular proteins.

D. Target Protein

NAZ domain functions as an independent module when appended to diverse proteins via the linker and therefore is a suitable reagent useful for directing degradation of a target protein.

The target protein is any protein containing a degradation regions required for cooperation with the NAZ domain. To induce degradation of said target protein, NAZ domain requires cooperation with the degradation region located on the target protein.

The target protein is any protein which contains degradation domain which makes it, per se, already more or less unstable. Most intracellular proteins important for cellular regulation are, under appropriate cellular conditions, subject to rapid intracellular degradation and are therefore not very stable.

Additionally, in the stable target proteins the degradation region may be induced via genetic manipulation or may be incorporated into NAZ-linker protein.

E. Modes of Preparation of Dual-Function Proteins For Selective Targeted Protein Degradation All modes of preparation of dual-proteins for selective targeted protein degradation essentially consist of the NAZ domain comprising at least 30 amino acids which are located within NAZ domain amino acids 55–84, or a corresponding degradation directing domain and the linker domain attached covalently or noncovalently.

Any mode of action by which these agents can be prepared using methods known in the art or those which will become available are intended to be within the scope of this invention.

F. Mode of Action For Selective Targeted Protein Degradation

A dual-function protein for selective targeted protein degradation prepared according to the invention, is complexed with the target protein by binding through the linker domain. The target protein which is susceptible to binding with the linker domain of the dual-function protein typically contains its own degradation region.

Basic Scheme of the Selective Targeted Protein Degradation

NAZ domain+Linker domain

NAZ-Linker+Target protein

NAZ-Linker–Target protein

NAZ-Linker remains+Target Protein Destroyed

Any modification of this process is intended to be within the scope of the invention. For example, the endogenous NAZ may be delivered as a degradative signal to several different targets via its natural association with a different linker. This approach allows combinatorial control by introducing NAZ-linker$_1$, NAZ-linker$_2$, etc., within a single class of cells suitable for destruction of different target proteins.

These and other modifications of the method are intended to be within the scope of invention.

II. In Vitro Studies For Selective Targeted Protein Degradation

The concept of the targeted degradation was first developed and tested in vitro. These studies are described in detail in U.S. Pat. No. 5,866,121 issued on Feb. 2, 1999, incorporated herein by reference.

Background studies for the current invention include confirmation that antizyme association with ornithine decarboxylase promotes ornithine decarboxylase degradation and that there exist two distinct antizyme domains for association and degradation of proteins.

A. Antizyme Association With OD Promotes OD Degradation in Mammalian Cells

The first studies leading to the current invention confirmed that the mammalian (mouse) and flagellate parasite (*Trypanosoma brucei*) ODC are different enzymes. While the mouse ODC is selectively degraded in the presence of polyamines and its concentration within mouse cells thus seems to be regulated by cellular polyamine levels, the *Trypanosoma brucei* ODC is not dependant upon or regulated by polyamines.

The first series of background studies, described in *Mol. Cell. Biol.*, 12: 3556–3562 (1992), addressed differences between intracellular degradation of mammalian (mouse) and parasitic flagellate (*Trypanosoma brucei*) ornithine decarboxylase (ODC).

The mouse ODC is known to be regulated by intracellular polyamines, and mammalian ODC was found to be selectively degraded by cells when polyamines level increased. The *Trypanosoma brucei* ODC is not regulated by intracellular polyamines and degradation of this protein is not dependent on polyamines. The *Trypanosoma brucei* and mouse ODS are therefore different enzymes.

When this finding was tested vis-a-vis antizyme, it was found that antizyme, a reversible tightly binding protein inhibitor of mouse ODC, was involved in the mouse ODC degradation process but was not involved in degradation of *Trypanosoma brucei* ODC. While mouse ODC was found to interact with antizyme in vitro, unmodified *Trypanosoma brucei* ODC does not interact with antizyme. Thus, the polyamine-mediated decrease of ODC activity in mammalian cells seems to be somehow associated with the presence of a polyamine-induced protein antizyme. It was further discovered that antizyme is capable of binding mammalian ODC and reversibly inhibiting its enzymatic activity. However, antizyme itself and alone does not and is not capable of degrading ODC. Clearly, another component is needed to achieve mammalian ODC degradation.

Antizyme promotes degradation of mammalian ODC by forming a binding complex with ODC and then acting in some way to promote its degradation. The difference between the polyamine regulation of mouse ODC and trypanosomal ODC seems to be associated with ODC sensitivity toward and ability to bind to antizyme. When the region of mouse ODC between amino acids 117 and 140 necessary for antizyme binding was identified and tested, the constructs containing this region were shown to be inhibited and precipitated by antizyme in vitro. Replacing the mouse 117–140 amino acid region with the corresponding 117–140 amino acid region from *Trypanosoma brucei* ODC converted mouse ODC into a form resistant to antizyme in vitro and made it unresponsive to polyamines in vivo.

These studies show that antizyme binding to a certain specific region of ODC promotes degradation of ODC and imply that interaction between antizyme and ODC is a necessary step in polyamine-induced degradation. The amino acid region between amino acid 117 and 140 of the vertebrate ODC is the antizyme-binding region.

Conclusion of this initial study was that ODC possesses a very specific amino acid region located between 117–140 amino acids of the 461 amino acid mouse ODC sequence which is responsible for antizyme-ODC binding. When this region is present within ODC, as in vertebrates, the antizyme-ODC binding occurs. When this region is not present or is not substantially identical to that found in vertebrates, such antizyme-ODC binding does not occur. Replacement of one region for another can either promote or prevent antizyme-ODC binding and affect in vivo regulation. Formation of antizyme ODC binding complex is therefore necessary for regulated degradation of ODC. Such binding can only be achieved when the specific binding region on ODC is present.

B. Antizyme Domains For Association and Degradation of Proteins

In the second series of background studies, described in *Mol. Cell. Biol.*, 13: 2377–2383 (1993) and ibid, 14: 87–92

(1994) the domains responsible for possible interaction between antizyme and a binding element of ODS were investigated. The studies determined that such interaction are essential but not sufficient for regulation of the ODC by polyamines. These studies additionally determined that while the binding element of ODC is present near the ODC N-terminus, a second element present at the ODC C-terminus is also required for the degradation process and that antizyme somehow causes a conformational change in the ODC. This conformational change makes the C-terminus of ODC more accessible.

These findings were confirmed by inhibition studies where, when the C-terminus was blocked with antibody, the degradation was prevented. Tethering the C-terminus by a circularly permuted, enzymatically active form of ODC also prevented antizyme-mediated degradation.

These studies have clearly shown that there are two distinct successive stages of antizyme-directed degradation. The first stage requires only the association of antizyme and ODC. This results in catalytic inactivation of ODC and exposure of the C-terminus, demonstrated by increased access to antibody specific for the 376-to-461 region. The change in conformation induced by antizyme is not, however, sufficiently global to produce a readily detectable change in the rate or pattern of fragmentation produced by protease. The second stage encompasses proteolytic degradation per se.

These studies show that C-terminal domain of antizyme alone is only able to inactivate ODC and alter its conformation, but it is not able to direct degradation of the enzyme, either in vitro or in vivo. For that, the N-terminal domain of antizyme must be present.

These prior studies determined that similarly to ODC, antizyme also consists of two distinct domains, both of which are required for binding and proteolysis of ODC. These domains differ from two regions found to be present on ODC.

III. A Selective Targeted Protein Degradation

The studies described in Sections IIA and IIB show that the degradation of ornithine decarboxylase (ODC) is mediated by its association with the inducible protein antizyme and that the N-terminus of antizyme (NAZ), although unnecessary for the interaction of antizyme with ODC, is necessary to induce ODC degradation.

On the basis of the previous findings, the studies were undertaken to investigate whether the antizyme may assert the similar degradative properties on the other heterologous intracellular proteins.

In the follow-up studies leading to this invention, it was surprisingly discovered that a covalent fusion of N-terminus domain of antizyme (NAZ) to other target proteins results in the liability of these proteins and in their destruction. Such liability was previously known to exist only during the non-covalent association of native antizyme and ODC.

1. NAZ and Its Function in Degradation of Proteins

To determine whether the function of NAZ domain is specific only for ODC or whether it could act in a similar fashion as a general modular function domain when grafted to other heterologous proteins, recombinant DNA constructs were prepared and used in studies described below.

Results of studies leading to and resulting in the discovery of targeted degradation of proteins in situ are illustrated in FIGS. 1–13.

A. Degradation of Mouse ODC is Induced Solely By NAZ Domain Without Presence of CAZ Domain To test whether N-terminus domain of antizyme (NAZ) alone, without the presence of the C-terminus domain of antizyme (CAZ), can promote ODC degradation, recombinant DNA fusion constructs of mouse ODC with NAZ domain (NAZ-MODC) were prepared according to Example 7.

Mouse ODC (MODC) is relatively stable protein in an in vitro degradation system derived from rabbit reticulocytes. Its degradation, however, is promoted and enhanced by the addition of the regulatory protein antizyme. As described above, antizyme is known to contain two functionally distinguishable domains. The C-terminus domain of the protein (CAZ) binds to ODC, whereas the N-terminal part of antizyme (NAZ) has capability to direct degradation of ODC in vitro or in vivo.

To determine whether the NAZ domain is solely responsible for protein degradation or whether the C-terminus (CAZ) domain is also necessary, a portion of antizyme, specifically amino acids 1–97 of antizyme N-terminus was fused to MODC to make fusion protein NAZ-MODC. Results are seen in FIG. 1.

FIG. 1 shows in vitro degradation of mouse ODC induced by fusion of amino acids 1–97 of NAZ domain to mouse ODC (MODC). As a control, the C-terminus (amino acids 106–212) of antizyme (CAZ) was also fused to MODC to make CAZ-MODC. The fusion proteins seen in FIG. 1 were subjected to degradation for 0, 1, and 2 hours. The position of migration of each protein is indicated by arrow.

The time course of in vitro degradation of [$^{35}$S]-methionine labeled proteins was examined and the labeled proteins remaining undestroyed after the indicated period of incubation were determined by SDS-PAGE and autoradiography.

FIG. 1A shows structures of antizyme and fusion proteins NAZ-MODC and CAZ-MODC. Antizyme N-terminal half (NAZ) is depicted as a solid block. Antizyme C-terminal half (CAZ) is depicted as a fine cross-hatch block. MODC is depicted as a coarse cross-hatch block.

FIG. 1B shows MODC fused to the C-terminal half of antizyme to form CAZ-MODC fusion protein or to the N-terminal half of antizyme to form NAZ-MODC fusion protein. As seen from FIG. 1B, NAZ-MODC fusion protein was gradually destroyed with time and was largely degraded in 2 hours. In contrast, the CAZ-MODC fusion protein was stable and no degradation was observed during the same time when the NAZ-MODC was degraded. The fusion construct NAZ-MODC contains the two domains needed for ODC degradation, that is the NAZ domain and the mouse ODC C-terminus. CAZ-MODC does not contain NAZ domain. NAZ domain alone was, therefore, shown to be responsible for the degradation of ODC. When provided with a means to associate with its target, whether that association is non-covalent as with intact antizyme, or covalent as in the AZ-MODC fusion protein, NAZ domain was capable to direct the ODC protein degradation.

In conclusion, results of this study show that NAZ, when coupled directly to ODC by way of fusion constructs, is solely responsible for antizyme NAZ domain degradative capability.

B. Two Functional Domains Jointly Direct Degradation of Trypanosomal ODC

Ornithine decarboxylase from *Trypanosoma brucei* (TbODC), although almost 70% identical to MODC in its core structure, is a stable protein. TbODC is insensitive to regulation by polyamines in the native context of the parasite or when expressed in mammalian cells. It lacks both the C-terminal degradation domain and the antizyme-binding domain present in the mouse ODC. The protein can be converted into one that is unstable in vivo, but still unresponsive to polyamines, by replacing its C-terminus with the degradation domain of mouse ODC. Such conversion has been done by preparing chimeric proteins, in which a junction between mouse and trypanosomal ODC, without insertion or deletion, was created at amino acid 376 to make a Tb376M or at 422 to make Tb422M, as shown in FIG. 2A.

To test whether NAZ domain can destabilize otherwise stable proteins and promote degradation in a protein which is insensitive to polyamines and not subject to antizyme induced degradation, recombinant DNA fusion constructs of NAZ domain with alchemeric protein Tb367M (NAZ-Tb367M) were prepared. Tb367M is a chimeric protein in which a junction between mouse and Trypanosoma brucei ODC (Tb376M) was created at 367 amino acid. NAZ-Tb367M was prepared according to Example 6. Results are shown in FIG. 2.

FIG. 2 shows TbODC degradation induced by the incorporation of N-terminus of antizyme (NAZ) into a construct consisting of ODC and C-terminus of mouse ODC.

To test whether NAZ domain was capable of inducing Tb376M degradation in vitro, NAZ domain was coupled with the TbODC, Tb422M and Tb376M protein, to generate chimeric fusion constructs. Structures of these constructs are seen in FIG. 2A.

FIG. 2A shows structures of trypanosomal ODC (TbODC, FIG. 2A-1), Tb376M (FIG. 2A-2) and Tb422M (FIG. 2A-5) chimeras and the fusion constructs of NAZ domain with Trypanosomal ODC (NAZ-Tb ODC, FIG. 2A-3), with mouse C-terminal domains containing amino acids 376–461 (NAZ-T376M, FIG. 2A-4) or 422–461 (NAZ-Tb422M, FIG. 2A-6). TbODC is depicted as an open block. NAZ domain is depicted as a solid block. MODC C-terminus is depicted as a cross-hatched block.

Results of degradation analysis of chimeric proteins TbODC, T376M alone, NAZ-TbODC and NAZ-Tb376M are seen in FIG. 2B.

In vitro degradation analysis illustrated in FIG. 2B showed that NAZ-Tb376M was gradually degraded during the two hours and that both NAZ domain and the C-terminus of mouse ODC were needed to induce efficient degradation of TbODC. Neither the C-terminus domain of mouse ODC alone attached to TbODC (T376M) nor NAZ domain attached to TbODC (NAZ-TbODC) were capable of changing the stability of TbODC. Densitometric analysis of the data of FIG. 2B is displayed as FIG. 2C.

FIG. 2C shows quantitation of degradation of TbODC. As seen in FIG. 2C, the incorporation of NAZ into NAZ-Tb367M chimeric protein resulted in more than double degradation.

Degradation of protein with NAZ domain was not limited to the Tb376M but was also observed for Tb422M protein. Results are seen in FIG. 2D. As seen in FIG. 2D, NAZ domain also stimulated the degradation of Tb422M. NAZ-Tb422M contains the entire open reading frame of trypanosomal ODC except for the last 2 amino acids, sandwiched between NAZ domain and the C-terminus (amino acids 422–461) of mouse ODC.

The studies described above show that both functional domains, that is NAZ domain and the C-terminus domain of the ODC are necessary and sufficient to cause in vitro destabilization and degradation of a stable Trypanosomal ODC protein.

To determine whether antizyme-mediated degradation of ODC by the 26S proteasome is independent of ubiquitination, the studies were designed to examine whether degradation induced by appending NAZ domain involves ubiquitin modification. In these studies, NAZ-Tb376M and NAZ-Tb422M were incubated as for in vitro degradation, but ATP was substituted with ATP-γ-S. ATP-γ-S has been previously shown to block degradation but not ubiquitination (Cell, 63: 1129–1136 (1990)), thereby leading to the accumulation of high molecular weight forms of a target protein decorated by multiple ubiquitin chains.

FIG. 3 illustrates effect of ATP-γ-S on degradation of NAZ-Tb376M and NAZ-Tb422M proteins.

In FIG. 3A, proteolysis was induced by co-incubation of oncoprotein p53 with human papilomavirus 16 E6 (left three lanes) or by fusion of NAZ domain to Tb376M or to Tb422M (right six lanes). Samples were analyzed at time 0 or after 2 hours of incubation. As indicated, reactions were performed with ATP or replacing ATP with ATP-γ-S.

As seen in FIG. 3A, both NAZ-Tb376M and NAZ-Tb422M were degraded in the presence of ATP. Substitution of ATP-γ-S for ATP blocked degradation, but high molecular weight conjugates of NAZ-Tb376M and NAZ-Tb422M did not appear. As a positive control, HPV16 E6-mediated degradation of p53 which is ubiquitin dependent, was used. In the presence of E6 and ATP, p53 was degraded. When ATP-γ-S was used instead of ATP, degradation was blocked and high molecular weight forms of p53 accumulated.

Figure 3B:
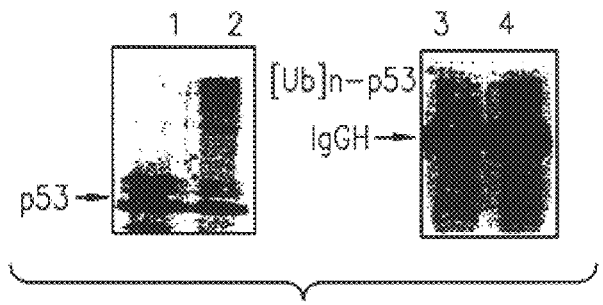

In FIG. 3B, the composition of conjugates produced as in FIG. 3A was tested by immunoprecipitation with anti-p53 antibody PAb421, followed by separation on SDS-PAGE, and autoradiography (lanes 1 and 2), or by transfer to nitrocellulose paper and immunodetection with anti-ubiquitin antibody (lanes 3 and 4). Lanes 1 and 3 show p53 incubated without the presence of E6. Lanes 2 and 4 show p53 incubated with E6 and ATP-γ-S. The position of the high molecular weight ubiquitin conjugates and of the IgG heavy chains reactive with the secondary antibody is indicated between lanes 2 and 3.

As seen in FIG. 3B, immunoprecipitation with a monoclonal antibody to p53 (PAb42) followed by Western blot analysis using anti-ubiquitin antiserum confirmed that the high molecular weight proteins enhanced in the presence of ATP-γ-S consisted of poly-ubiquitinated p53.

These results show that NAZ-induced degradation of NAZ-Tb376M and NAZ-Tb422M, like antizyme-mediated degradation of ODC, is ubiquitin independent.

C. The Destruction Box of Cyclin B Cooperates with NAZ Domain in Protein Degradation To test whether other short-lived proteins can confer liability on the otherwise stable TbODC protein, the cyclin B degradation domain within amino acids 13–90 was fused to the C-terminus of TbODC. Results are seen in FIG. 4.

Sea urchin cyclin B is well-characterized short-lived protein that accumulates at interphase and is degraded at metaphase. Degradation of the protein allows cells to exit metaphase and enter interphase. The protein is stable in frog oocyte extracts prepared from interphase cells, but it is rapidly degraded in metaphase extracts. The specific capacity of mitotic cell extracts to degrade cyclin B thus reproduces faithfully the property of the cell of origin. Degradation of cyclin B was previously (Nature, 349:132–138 (1991)) shown to require that it contain both ubiquitination sites and a destruction box. Its N-terminus contains all the structural information needed for degradation. Its amino acid 13–90 region fused to staphylococcal protein A is able to induce degradation in metaphase cell extracts. A smaller region, amino acids 13–59, does not contain the ubiquitination sites and does not undergo proteolysis, presumably because the lysines within amino acids 60–66 are not present to serve as ubiquitin modification sites. Likewise, a single mutation at the conserved arginine in the destruction box (amino acids 42–50), a conserved region in the N-terminus, prevents cycle-specific degradation.

In these studies, NAZ domain was fused to two amino acid regions of cyclin B protein which has been shown to contain two region in its N-terminus. The region of cyclin $B_{13-90}$ (amino acids 13–90) is capable of undergoing degradation when fused to Protein A. The other region of cyclin $B_{13-59}$ (amino acids 13–59), is not subject to such degradation.

To test whether the cyclin B degradation domain within amino acids 13–90 can confer liability on the otherwise stable TbODC, this region was fused with C-terminus of TbODC in the presence or in the absence of NAZ domain.

FIG. 4 shows NAZ-induced degradation of TbODC-cyclin $B_{13-90}$, with ubiquitination sites, and TbODC-cyclin $B_{13-59}$, without ubiquitination sites.

Figure 4A:
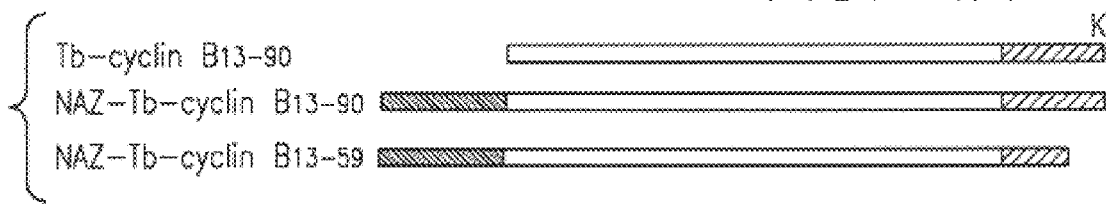
FIG. 4 illustrates NAZ-induced degradation of TbODC-cyclin B 13–90 (with ubiquitination site) and TbODC-cyclin B 13–59 (without ubiquitination site).

FIG. 4A shows a structure of Tb-cyclin $B_{13-90}$, NAZ-Tb-cyclin $B_{13-90}$ and NAZ-Tb-cyclin $B_{13-59}$ fusion proteins. NAZ domain is depicted as a solid block. TbODC is depicted as an open block. Cyclin B is depicted as a hatched block. The region of cyclin $B_{13-90}$ containing lysines that are the ubiquitination sites of cyclin B is marked "K".

Figure 4B:
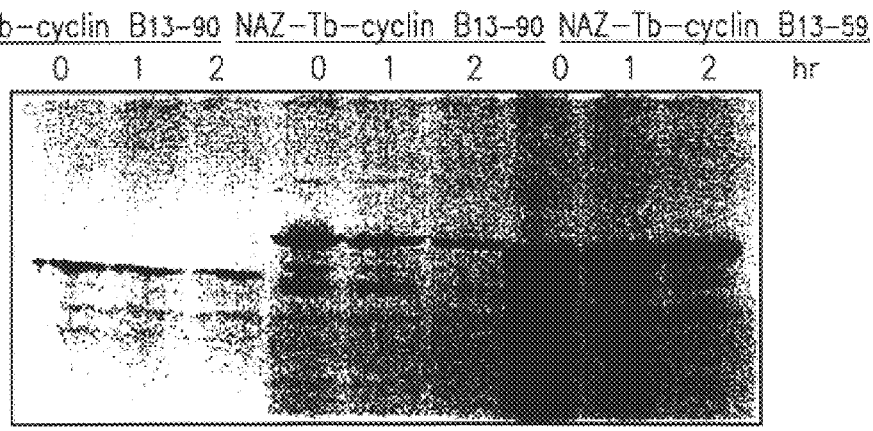

FIG. 4B shows Tb-cyclin $B_{13-90}$, NAZ-Tb-cyclin $B_{13-90}$ and NAZ-Tb-cyclin $B_{13-59}$ which were subjected to degradation under the conditions described above. The results were analyzed as described in FIG. 1.

As shown in FIG. 4B, the TbODC-cyclin $B_{13-90}$ fusion protein containing ubiquitination sites was stable in the reticulocyte lysate. These results agreed with the conclusion that this portion of cyclin alone cannot promote degradation of protein A. However, the TbODC-cyclin $B_{13-90}$ fusion protein becomes unstable after NAZ domain was appended to form NAZ-TbODC-cyclin $B_{13-90}$. Furthermore, deleting the lysine residues that are putative sites of ubiquitination from NAZ-TbODC-cyclin $B_{13-90}$, to form NAZ-TbODC-cyclin $B_{13-59}$, did not alter its degradative properties.

The association of these regions of cyclin B with NAZ domain made both NAZ-cyclin $B_{13-90}$ and NAZ-cyclin $B_{13-59}$ unstable and subject to degradation. Furthermore, NAZ-cyclin $B_{13-59}$ construct was able to induce in vitro degradation of *Trypanosoma brucei* ODC, a stable protein.

These results confirm that cyclin B amino acids 13–59 contains a domain that can cooperate with NAZ domain to promote trypanosomal ODC degradation in vitro. Such degradation is independent of the presence of lysine residues contained within amino acids 60–90, which are the normal targets for ubiquitination, further confirming that NAZ domain can provide an alternate signal for degradation that bypasses the requirement for ubiquitin modification.

To test whether the NAZ domain has a capability to directly induce degradation of the cyclin B degradation region 13–90 in a rabbit reticulocyte lysate, NAZ domain was coupled with amino acids 13–90 or amino acids 13–59. Results are seen in FIG. 5.

FIG. 5 illustrates NAZ-induced degradation of NAZ-cyclin $B_{13-90}$ (with ubiquitination sites) and NAZ-cyclin $B_{13-59}$ (without ubiquitination sites). Unfused cyclin $B_{13-59}$ was used as control.

FIG. 5A shows a schematic structure of NAZ-cyclin fusion proteins. NAZ domain is depicted as a solid block. Cyclin B is depicted as a hatched block.

In studies shown in FIG. 5B, the proteins were subjected to degradation according to Example 8 and results were analyzed as previously described. As seen in FIG. 5B, both fusion proteins NAZ-cyclin $B_{13-90}$ and NAZ-cyclin $B_{13-59}$ were degraded while the control cyclin B 13–59 remained intact.

FIG. 5C shows quantitation of degradation of above fusion proteins. Triangles represent cyclin B 13–90 used as a control. Open circles represent fusion construct NAZ-cyclin B 13–90. Solid circles represent fusion construct NAZ-cyclin B 13–59. Fusion constructs, NAZ domain containing proteins, were quantitatively destroyed about twice as fast as the control proteins.

As expected for a metaphase-specific substrate subjected to degradation in the reticulocyte-based degradation assay system, the cyclin B degradation region 13–90 alone used as a control was relatively stable and did not lead to protein degradation. NAZ domain, on the other hand, was able to direct the degradation of both fusion proteins, regardless of presence or absence of ubiquitination sites.

NAZ domain therefore can alter the degradation properties of cyclin B amino acids 13–90 in two ways, by promoting its liability in the absence of cycle specific signals and by diverting it to a pathway that does not require ubiquitination.

D. Identification of Degradation Region of the Target Protein That Confers Liability In order to determine which region of the NAZ domains, antizyme or the target protein confers liability, the series of additional studies were performed.

As was seen in prior sections, for degradation of the target protein to occur, two elements are necessary to be present, namely the antizyme binding region where the C-terminal domain of the antizyme attaches antizyme to the protein directly or to the intermediary linking region and the NAZ-degradation region where the N-terminal domain of antizyme causes target proteins degradation. The N-terminus half of antizyme is thus not involved in the antizyme/target protein interaction, but it is required for the target protein degradation. Because NAZ domain is a functional module that only functions when attached to the target protein, identification of a domain within target protein which cooperates with NAZ domain was investigated.

For these studies, a labile p53 protein was selected as a candidate.

Tumor suppressor protein p53 imposes negative regulation on the cell cycle, and abnormal inactivation of the protein has been shown to be related to cell transformation and tumorigenesis. Elimination of p53 protein negative regulation may be achieved by degradation, interaction with other proteins, interaction with mutant forms of p53 itself, or with somatic or germline mutation. Degradation of p53 is influenced by protein-protein interactions. A variety of viral oncoproteins have been shown to act on p53. The association of p53 with SV40 large T antigen or with adenovirus 2 E1B-55K protein extends its half-life, but the association with E6 protein of human papillomavirus (HPV) 16 shortens the half life. Mutation of p53 can change its function and stability. The multiple influences that can play on p53 stability make its degradation a suitable subject for study of effect of NAZ attachment to p53 degradation domain.

Normal degradation of p53 is mediated by the ATP-dependent and nonlysosomal large 26 S protease complex. Ubiquitination is required for p53 degradation. E6 and the associated host cell protein E6-AP act as a ubiquitin ligase E3, which leads to ubiquitination of p53 protein and its degradation. The structural elements of p53 needed for recognition and destruction by the proteolytic machinery remain unclear, as is true for most short-lived proteins.

For the 26 S protease to act and destroy the target protein, the target protein must contain a structural motif, so called a degradation region. In order to undergo protein degradation, whether via ubiquitin-dependent or ubiquitin-independent pathways, this region is required.

In the studies described below, a degradation region of p53 was identified by fusing it to NAZ domain and making deletions within the p53 moiety. The identified degradation region of p53 was able to function similarly to the degradation region of mouse ODC. Like the degradation region of mouse ODC within the fusion protein consisting of NAZ-ODC, p53 fused to NAZ domain was able to induce degradation of trypanosomal ODC, otherwise a stable protein.

E. Identification of the p53 Degradation Domain

To determine if p53 has a region that can collaborate with NAZ domain, NAZ domain was fused directly to p53 and the liability of NAZ-p53, as well as a series of deletions within the 393-amino acid p53 moiety of the NAZ-p53 fusion construct molecule were analyzed. Deletions were made from each end or from both ends. Results are seen in FIGS. 6 and 7.

Figure 6:
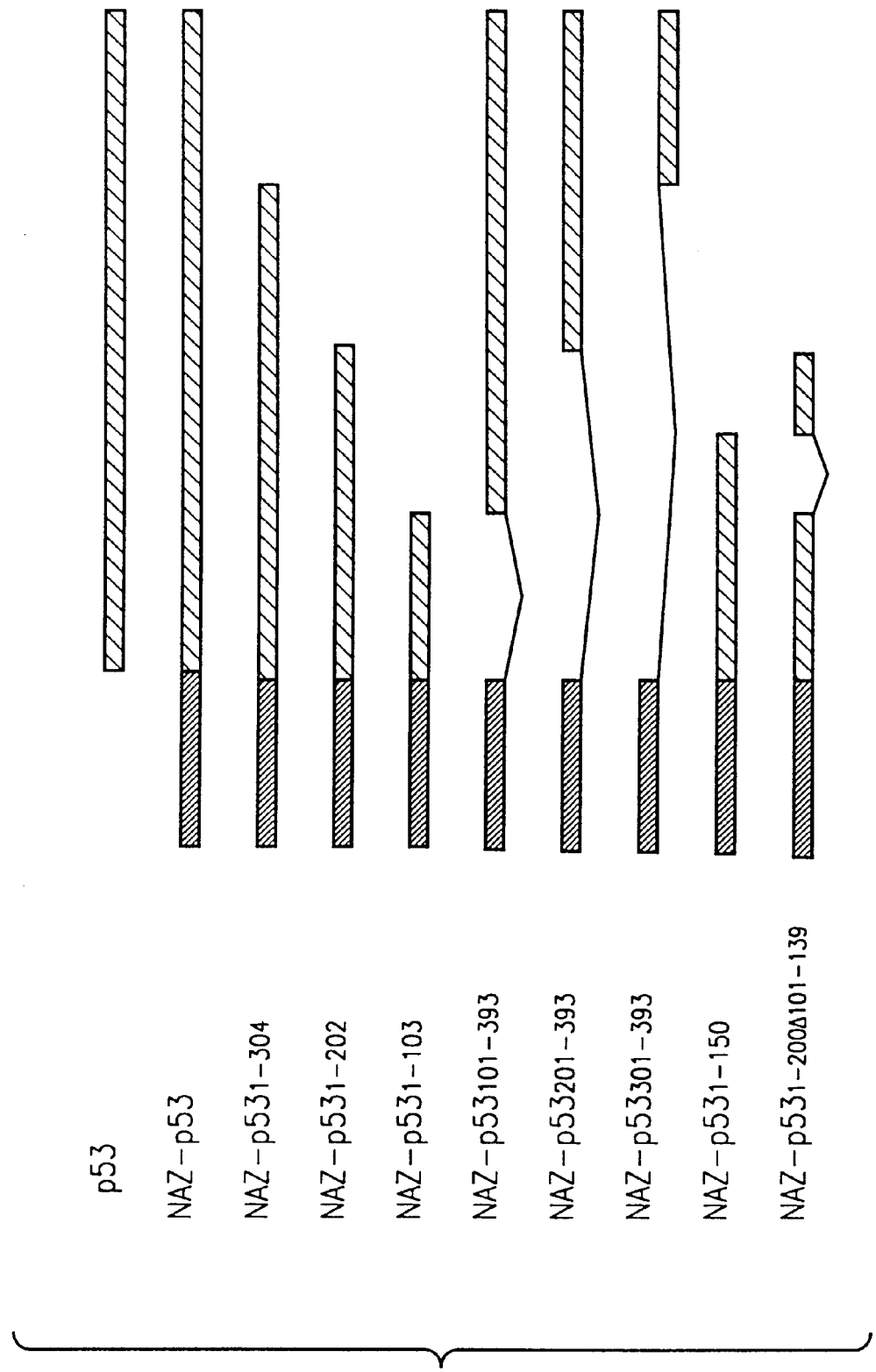
FIG. 6 shows structure of NAZ-p53 and deletions of p53 moiety.

FIG. 6 shows structure of entities depicting p53 protein, NAZ-p53 fusion construct, NAZ-p53 fusion protein fragments 1–304, 1–202 and 1–103 and numerous deletions of p53 moiety. Deletions were made from each end or from both ends. NAZ is depicted as a solid block; p53 is depicted as a hatched block. Entities depicted in FIG. 6 were submitted to NAZ domain induced degradation illustrated in FIGS. 7A–D.

Figure 7A:
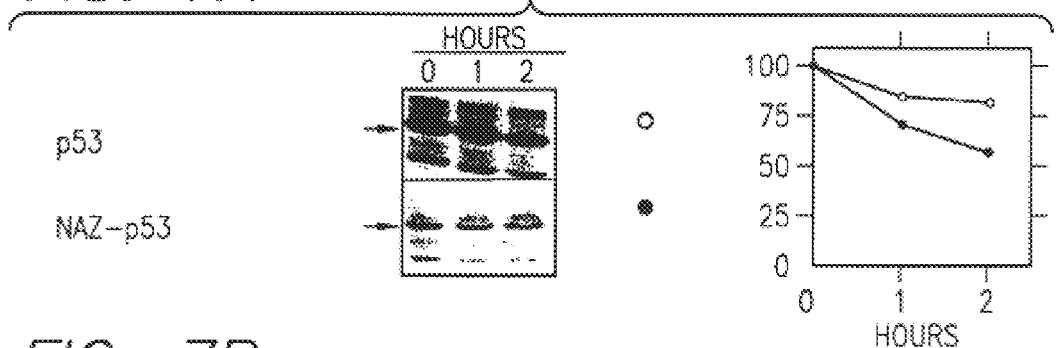
FIG. 7 illustrates NAZ-induced degradation of p53.

FIG. 7A shows degradation pattern of p53 and NAZ-p53. As seen in FIG. 7A, there was slight degree of degradation of p53 observed using the degradation conditions described in Example 8. Under the same conditions, NAZ-p53 was degraded about twice as fast.

Figure 7B:
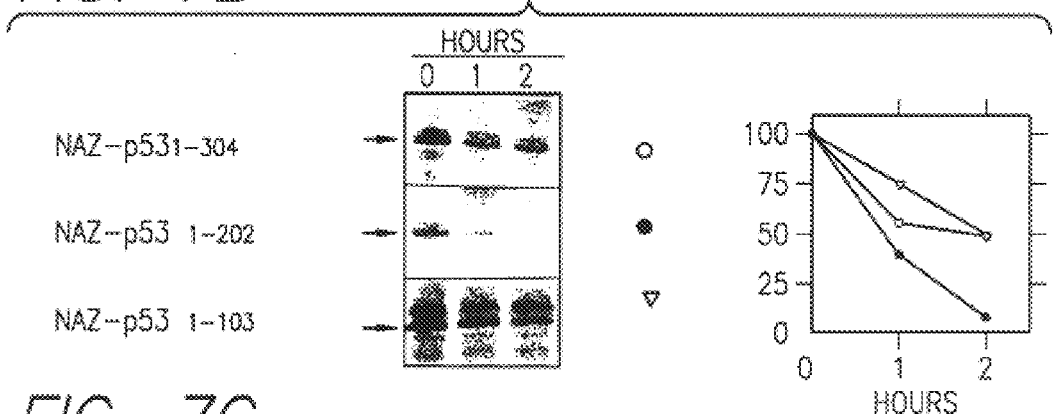

FIG. 7B shows degradation pattern of fusion protein entities containing the C-terminal deletions of p53, namely NAZ-p53 1–304, NAZ-p53 1–202, and NAZ-p53 1–103. As seen in FIG. 7B, both NAZ-p53 1–304 and NAZ-p53 1–103 were degraded by about 50% at two hours. NAZ-p53 1–202, on the other hand was almost completely degraded during the same time.

Figure 7C:
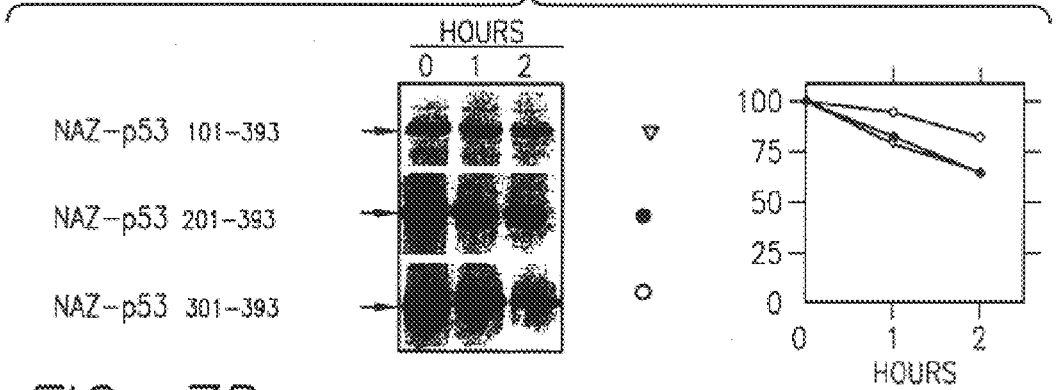

FIG. 7C is shows degradation pattern of fusion protein entities containing the N-terminal deletions of p53, namely NAZ-p53 101–393, NAZ-p53 201–393, and NAZ-p53 301–393. As seen in FIG. 7C, N-terminus deletions of p53 resulted only in small degree of degradation in all NAZ-p53 101–393, NAZ-p53 201–393 and NAZ-p53 301–393. Such degradation was qual to the degradation observed for p53 protein.

Figure 7D:
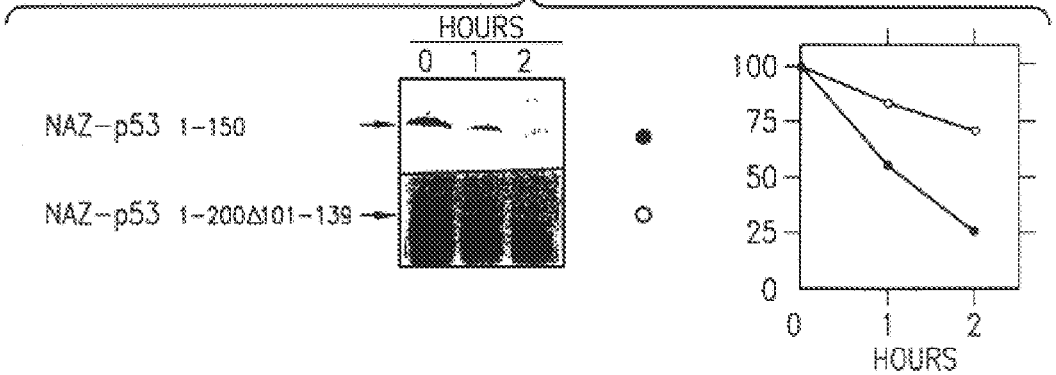

FIG. 7D shows a degradation pattern of fusion protein entity containing C terminal NAZ-p53 1–150 having removed amino acids 151–200 and entity containing internal deletion of p53, namely deletion of NAZ-p53 100–139 from NAZ-p53 1–200. As seen in FIG. 7B, the internal deletion of amino acids 100–139 increased a degree of p53 degradation to only about 30% compared to about 74% of degradation observed for NAZ-p53 1–150.

As seen in FIG. 7B, NAZ-p53 1–202 was found to be very extensively degraded and deleting 99 amino acids from its C-terminus (NAZ-p53 1–103) greatly stabilized it. Degradation of NAZ-p53 1–202 is more extensive than that of NAZ-p53, the parent molecule, or of NAZ-p53 1–304. This seem to occur because either amino acids 203–304 protect amino acid 103–202 region by altering its structure or denying access to a protease, or the degradation domain in p53 amino acid 103–202 region needs, like the degradation domain of mouse ODC, to be topologically at or close to the C-terminus of the antizyme.

The obtained results indicate that amino acids 101–202 of p53 protein contain a degradation domain. A more refined deletion from the C-terminus of p53 further demonstrated, as seen in FIG. 7D that removal of amino acids 151–202 from NAZ-p53 1–202 to form NAZ-p53 1–150 did not interfere with degradation, but the internal deletion of amino acids 101–139 from Δ NAZ-p53 1–200 to form NAZ-p53 1–200 Δ 101–139 prevented degradation.

These results show that p53 amino acids 100–150 region contains or is a degradation region of p53 that is active in a fusion with NAZ domain.

F. NAZ-mediated Degradation of P53$_{1-150}$ is Ubiquitin-Independent

To examine whether the NAZ-p53 fusion protein could in principle undergo degradation via a ubiquitinated intermediate, as is normal for p53, or by a ubiquitin-independent pathway, as is the case for ODC seen in FIG. 3, where it is shown associated with antizyme, in vitro degradation was carried out in the presence of ATP-γ-S. ATP-γ-S has been shown to block degradation but not ubiquitination. By grafting NAZ to p53, a fusion protein NAZp53 that is labile in vitro was created and deletion analysis was used to identify a degradation-determining region within p53. As a positive control, HPV16 E6-mediated degradation of p53, which is ubiquitin-dependent was used. Results are seen in FIG. 8.

Figure 8:
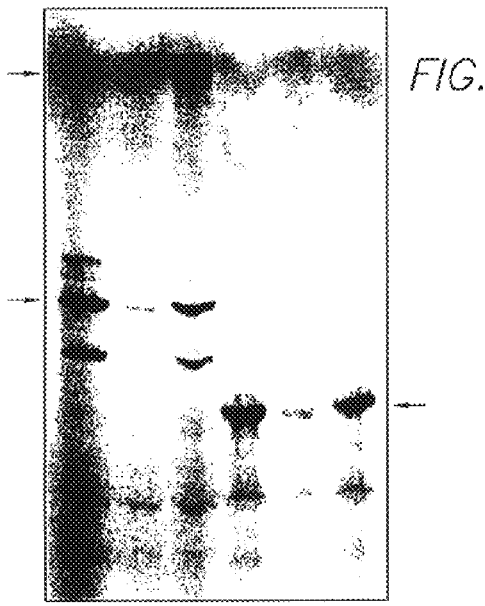
FIG. 8 shows effect of ATP-γ-S on p53 degradation.

FIG. 8 shows effect of ATP-γ-S on p53 degradation. Proteolysis was induced by non-covalent association of p53 with E6 (left three lanes) or by fusion of NAZ to p53 amino acids 1–150 (right three lanes), and the products of the reaction were analyzed by SDS-polyacrylamide gel electrophoresis and autoradiography. In both cases, time-dependent proteolysis occurred in the presence of ATP. When ATP-γ-S was used instead of ATP, proteolysis was inhibited in both cases. In the presence of ATP-γ-S, high molecular weight forms of p53 accumulated in the presence of E6 but not in its absence. Under identical conditions of incubation, no high molecular weight forms of NAZ-p53 1–150 were detected. Substitution of ATP-γ-S for ATP blocked degradation, but no high molecular mass form of the NAZ-p53 1–150 fusion protein appeared. It is clear that NAZ-induced degradation of p53 protein is ubiquitin-independent. The N-terminus of antizyme seems to bypass the modification normally required for p53 degradation and imposes instead its own properties otherwise associated with degradation of ODC.

G. A Monoclonal Antibody Blocks E6-mediated p53 Degradation

In this study, the degradation region, identified within the fusion proteins was investigated to show if it itself is involved in degradation of p53 itself by using a monoclonal antibody (PAb246) that specifically recognizes mouse p53 amino acids 88–109. Antibody PAb421 was used as a control. The PAb246 was used to determine whether it can block E6-mediated p53 degradation. Because there is no cross-reaction of the antibody with human p53 and because similarly directed antibodies to the human protein were not available, mouse p53 was used in this study. PAb246 recognizes the native conformation of p53 epitope. Results are seen in FIG. 9.

Figure 9:
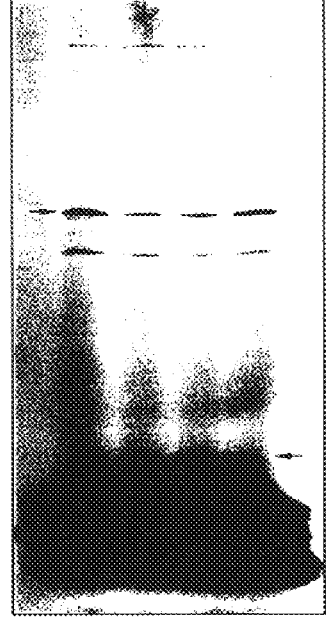
FIG. 9 illustrates effect of monoclonal antibody PAb246 specific for p53 amino acids 88–109 on E6-mediated degradation of mouse p53.

FIG. 9 shows the effect of monoclonal antibody PAb246 which is specific for p53 amino acids 88–109 on E6-mediated degradation of mouse p53. [$^{35}$S]-Methionine-labeled mouse p53 was subjected to degradation according to Example 8 in the absence of HPV16 E6 (Lane 1) and in the presence of E6 (Lanes 2–4). p53 was preincubated with control monoclonal antibody PAb421 (Lane 3) or with monoclonal antibody PAb246 (Lane 4).

As seen in FIG. 9, mouse p53 degradation was induced by human E6, but the presence of the antibody prevented this degradation. A control monoclonal antibody (PAb421)

against the C-terminus of p53, however, had no effect on degradation. These results show that the region of p53, identified as necessary for association with NAZ domain to lead to the protein degradation, must be accessible for that process to occur and that the epitope specific antibody can obstruct such access.

H. The Degradation Domain of p53 Induces Trypanosomal ODC Degradation

It was previously shown that the mouse ODC C-terminus is required for its in vivo degradation and that it confers liability on the homologous but stable ODC (TbODC) found in *Trypanosoma brucei*.

To find whether amino acids 100–150 of p53 contain the degradation domain which is similar in function to that disclosed in the mouse ODC C-terminus, the p53 100–150 region was fused to the C-terminus of TbODC to make TbODC-p53 100–150. ODC-deficient Chinese hamster ovary cells (C55.7) was stably transfected with TbODC-p53 100–150. The degradative activity of the TbODC-p53 100–150 fusion protein was determined by measuring the rate at which the ODC enzyme activity declined in cells where protein synthesis is inhibited with cycloheximide.

Measurement of ODC activity provides an accurate surrogate determination of its protein level. Results are seen in FIG. 10.

Figure 10:
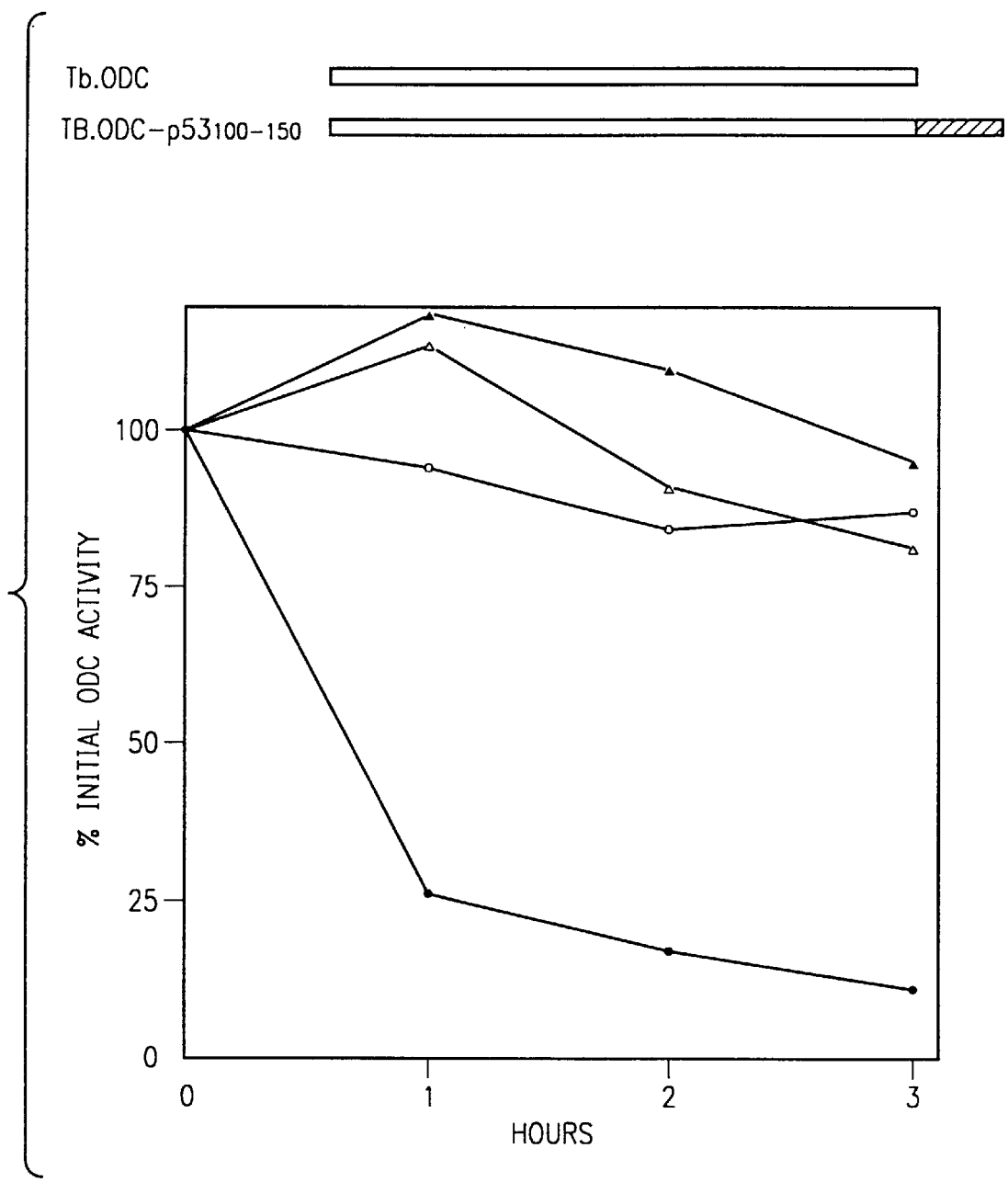
FIG. 10 shows effect of the p53 degradation domain (amino acids 100–150) on in vivo degradation of trypanosomal ODC.

FIG. 10 illustrates effect of the p53 degradation domain (amino acids 100–150) on in vivo degradation of trypanosomal ODC (TbODC). Components of TbODC chimeric proteins are depicted as open block. Components of p53 chimeric proteins are depicted as hatched blocks. Triangle represent TbODC activity, circles represent TbODC-p53 100–150 activity, solid symbols represent treated cells and open symbols represent untreated control cells. TbODC and TbODC-p53 100–150 initial activities were 51.0 and 15 pmol/mg/min, respectively. ODC stability in cells expressing TbODC or Tb-p53 100–150 was assessed by inhibiting protein synthesis with cycloheximide and determining residual enzymatic activity immediately and after 1, 2, or 3 hours. Control cells were similarly incubated, harvested, and analyzed but were not treated with cycloheximide. ODC activities are represented as a percentage of initial activity.

As seen in FIG. 10, ODC activity fell with a half-life of about 30 min. In contrast, the ODC activity provided by a construct encoding TbODC without the p53 degradation domain remained unaffected by cycloheximide treatment. These results shows that amino acids 100–150 of p53 in association with NAZ can confer in vivo liability on the stable protein TbODC.

I. The Degradation Domain of p53 Plus the Antizyme Binding Domain Confers Polyamine Regulation on Trypanosomal ODC To determine whether the degradation domain of p53 can cooperate with the antizyme binding domain to subject TbODC to polyamine-mediated degradation, a binding site for antizyme was provided. The N-terminus of the construct TbODC-p53 100–150 was replaced with an equivalent region of mouse ODC containing the antizyme binding domain to form M314T-p53 100–150.

For this study, cells were transformed as above and treated with the polyamine precursor putrescine for the indicated times to induce antizyme. ODC activity in the form of M314T-p53 100–150 was regulated by polyamines. Results are seen in FIG. 11.

Figure 11:
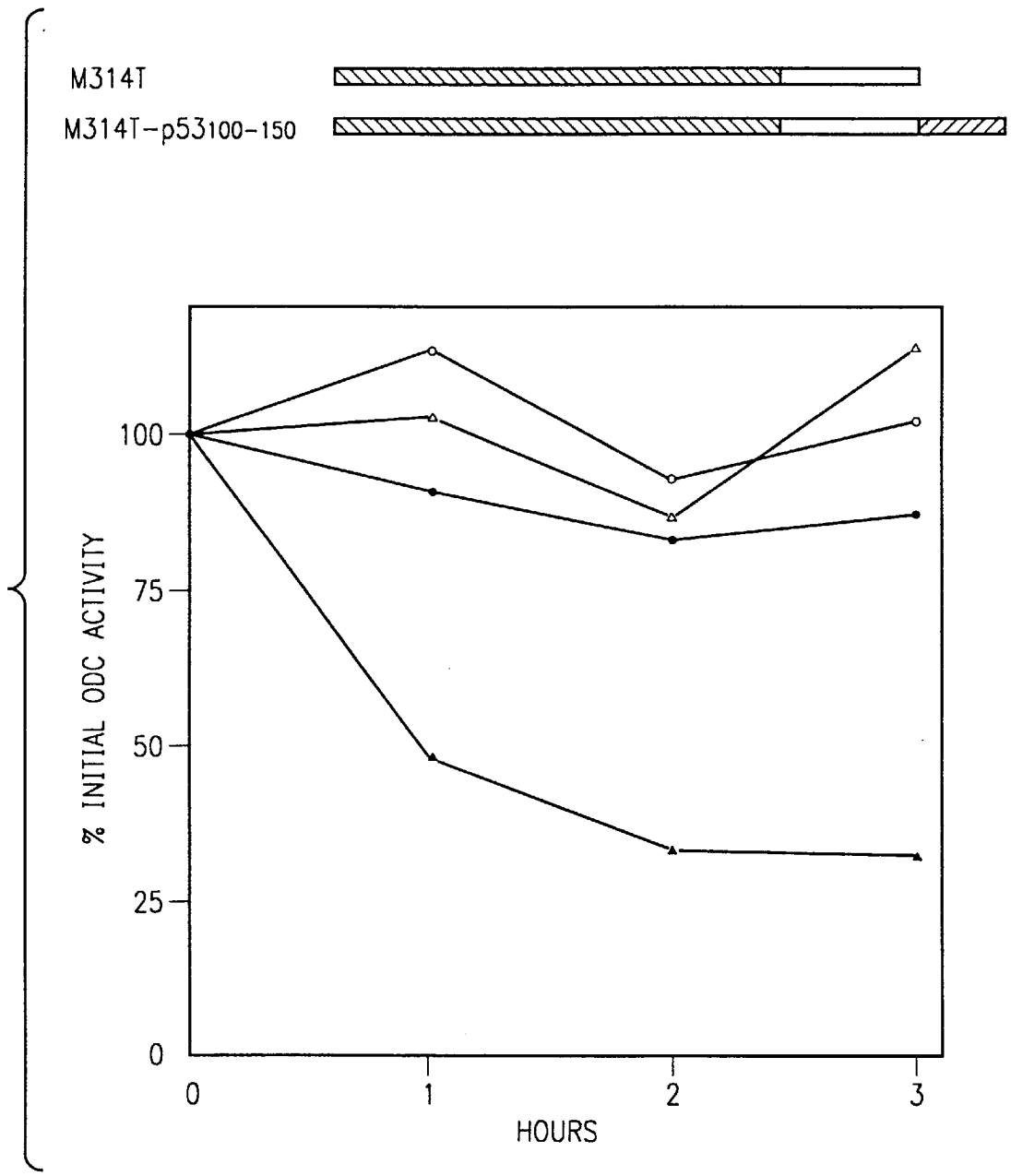
FIG. 11 shows effect of the p53 degradation domain (amino acids 100–150) on polyamine-dependent degradation of chimeric mouse/trypanosomal ODC (M314T).

FIG. 11 shows effect of the p53 degradation region amino acids 100–150, on polyamine-dependent degradation of chimeric mouse/trypanosomal ODC (MS14T). Components of TbODC chimeric proteins are depicted as open blocks. Components of mouse ODC chimeric proteins are depicted as cross-hatched blocks. Components of p53 chimeric proteins are depicted as hatched blocks.

To elicit polyamine-mediated regulation and induce endogenous antizyme, putrescine was added to the culture medium of cells expressing M314Tb or M314Tb-p53 100–150 to a final concentration of 100 $\mu$M. Cell lysates were prepared after the indicated time of treatment and assayed for ODC activity as described in *Mol.Cell Biol.*, 13:2377–2388 (1993). Control cells were similarly incubated, harvested, and analyzed but were not treated with putrescine. ODC activities are represented as the percentage of initial activity. M314Tb and M314Tb-p53 100–150 initial activities were 72.9 and 6.6 pmol/mg/min, respectively. M314T is depicted as circles. M314T-p53 100–150 is depicted as triangles. Treated cells are depicted as solid symbols. Untreated control cells are depicted as open symbols.

As seen in FIG. 11, within 4 hours of treatment ODC declined by about 65% from control values and subsequently remained at this level. However, M314Tb, identical to M314Tb-p53 100–150 but for the absence of the degradation domain of p53, was insensitive to regulation by polyamines. Therefore, p53 in this context can provide the same functional properties as the C-terminal degradation region of ODC.

In the above studies, NAZ-p53 protein constructs were utilized to find, using deletion analysis of the p53 moiety, whether these constructs would be labile. Results confirmed that these constructs would be labile but only if they contain amino acids 100–150 of p53. The domain containing amino acids 100–150 was identified as putative degradation domain of p53. The domain was able to destabilize trypanosomal ODC, as does the degradation domain of mouse ODS. Additionally, it was found that in mouse p53, E6-mediated degradation was blocked by an antibody specific for this region.

Previously, the mammal binding region of p53 for large T antigen targeting has been identified as amino acids 94–293. The degradation domain of p53, which was identified here, is located within this binding region. Therefore, the association of p53 with large T antigen could cover the degradation domain and prevent p53 degradation. Second, the findings are consistent with the distribution of mutations that increase the half-life of p53. Mutations in p53 are commonly found in tumors, and the mutated protein often has a much longer half-life than wild type p53. The mutations are widely distributed within the protein but are mainly located in four regions. One of the regions lies in the amino acid 100–150 degradation domain. Mutations in the region may either directly change the degradation domain itself to prevent protease targeting or change protein conformation to prevent ubiquitination.

K. Chemically Induced Dimerization

These results described above show that NAZ constitutes a functional domain that directs degradation when introduced into a suitable context. This supports the current discovery that conditional association of NAZ with protein targets directs their degradation, and that such degradation can be elicited by experimental manipulation of their association. This possibility is both as a way to further test how NAZ works and to develop a general means of cellular engineering that explored, has practical utility.

The system utilizes chemically induced dimerization system, described in *Science*, 262:1019 (1993). The system is based on the protein FKBP12 which is the cellular target of rapamycin, a potent immunosuppressor. This FKBP 12/rapamycin active complex, but neither of these two constituents alone, binds to the protein FRAP through the FKBP/rapamycin binding domain (termed FRB) of FRAP. FKBP12 and the FRB domain of FRAP therefore associate, but do so only in the presence of the ligand rapamycin, or its structurally related congener acting as a linker between FKBP12 and FRB. The experimental procedure is described in Example 12.

These studies support the general utility of the current invention as a viable therapeutic route to degrade, regulate and control the production of undesirable proteins and excessive production of proteins causing human and animal diseases.

IV. A Method for Selective Targeted Protein Degradation

A. Method For In Vivo Targeted Protein Degradation

A method for in vivo intracellular targeted protein degradation comprises in vivo and ex vivo genetic therapeutic approaches as well as in vivo gene therapy and ex vivo methods. The in vivo therapy according to the invention utilizes genetic modifications of the cells of a subject to be treated in order to combat disease caused by production or over production of a target protein. Such modifications may be induced in the cells in vivo by, for example, developing and providing a genetic material for expression of a specific dual-function protein targeting the undesirable protein within the cells, or it may be performed in the subject's own cells or other mammalian cells outside of the body, under ex vivo conditions. The resulting dual-function protein may be imported and delivered to the cells or tissue of the treated subject.

In vivo gene therapy consists of transferring the genetic material directly into the subject's cells.

Ex vivo gene therapy consists of removing cells from the subject and inserting the genetic material into these cells in vitro, prior to replacing the cells in the treated subject.

The method of the invention is particularly suitable for treatment of infectious disease by directing the dual-function protein against virus, bacterial or parasitic pathogen protein, against tumorigenic proteins produced by oncogenes or against a tumor suppressor gene proteins, against proteins secreted by a mutated gene and against protein involved in immune system disorders, such as against antigens causing allergies, inflammations or autoimmune diseases.

The method may be particularly useful in regulating inappropriately or excessively expressed proteins by a mutated gene by rapidly removing the excess protein from the cells.

A method for selected targeted protein degradation intracellularly in situ applicable for therapeutic purposes in vivo in mammalian subjects comprises the following steps:

a) identifying a target protein to be selectively destroyed;
b) identifying and selecting linker compound having a high specificity and high affinity to the target protein;
c) identifying the inhibitor of linker-target protein binding;
d) intracellularly inducing formation of antizyme and/or linker or delivering the antizyme or linker intracellularly or, in the alternative, extracelluarly inducing the synthesis of a dual-function protein, that is, a coupling of antizyme with the linker and delivering the dual-function protein intracellularly;
e) monitoring a degradative activity of the dual-function antizyme-linker fusion protein toward the target protein by measuring levels of the target protein in the cells; and
f) optionally inhibiting the degradative action of dual-function protein when the further degradation is no longer desired.

The identification of the target protein depends on the disease which is to be treated by the current method. For example, if the disease is hyperthyroidism where the disease is caused by the thyroid stimulators, that is proteins identified as thyroid stimulating antibodies, then these antibodies will become a target protein and the cells producing these stimulators will be treated.

If the target disease would be a tumorigenic growth, then the target protein would be a protein which is a product of oncogenic genes, as described below and the treated cells would be tumor cells.

A target protein is thus any protein which causes diseases or is a product of a disease and the treatment of the disease comprises a destruction of such target protein.

Selected target protein is then immobilized on the high affinity chromatography using a solid phase matrix, such as agarose, immobilization of the target protein. A mixture of various ligands is then used as a eluant and binding of the ligand to the solid phase is followed. Only those ligand binding to the target proteins are considered to become linkers. The ligand having the highest specificity and affinity is selected to become the linker between antizyme and target protein. Methods for high affinity chromatography are known and described, for example, in *Monoclonal Antibodies: Principles and Practice*, p. 111, J. W. Goding, Academic Press, Inc., New York (1983). The ligand may be a monoclonal antibody, an antigen, another protein and a chemical compound having a specific affinity for both the antizyme and the target protein, a receptor protein, etc, as long as it binds to antizyme and specifically recognizes the target protein and binds to it with high affinity.

The antizyme formation is then induced within the cells or delivered there. The antizyme, as described above, is conveniently induced by increased level of polyamines in the cells.

Polyamines are small organic polycations ubiquitous in living organisms. They are essential for cellular proliferation and development. The biochemical functions of polyamines are diverse. Optimal concentrations of polyamines benefit the fidelity and efficiency of in vitro transcription and translation reactions. This suggests that the rapid changes in polyamine pools observed in response to cellular signals for growth or differentiation are needed to optimize these biosynthetic processes. They are present in millimolar concentrations and are largely bound to RNA and DNA. Spermidine participates in a unique postranslational modification of the protein eIF-5A. Preventing that modification by genetic or pharmacological manipulation is lethal to cells.

Polyamine pools are regulated by biosynthesis, catabolism and transport. Their biosynthesis requires the concerted action of four enzymes: ornithine decarboxylase (ODC), S-adenosyl-methione decarboxylase, spermidine synthase, and spermine synthase. The initial and usually rate-limiting enzyme in the biosynthetic pathway is ODC. Expression of the ODC gene is rapidly induced by growth factors, hormones, and other stimuli. ODC activity is commonly elevated in cancer cells, and its forced expression can confer a cancer pheotype on some cells. Consequently, compounds that perturb polyamine pools and ODC inhibitors, in particular, have been identified as potentially useful for cancer chemotherapy, *Int. J. Oncol.*, 13:993 (1998).

Excess polyamines are toxic. Cells limit their levels by several means, controlling catabolism and transport as well as synthesis. One effect of raising polyamine levels is to sharply and quickly reduce the amount of ODC in cells. The induction of antizyme by polyamines is essential to this response in animal cells.

The subject of the treatment is pretreated, for example, with polyamine compounds such as spermine, spermidine, putrescine, cadaverine or their analogs in doses which increase antizyme production. Alternatively, the antizyme is produced extracorporally and delivered into the cells or tissue.

One preferred mode of delivering the antizyme into cells is by producing the antizyme-linker complex ex vivo in cells and delivering it by targeted delivery, such as encapsulated into liposomes, by infusion, etc., preferably to the organ or tissue cells where the target protein is found. The second and most preferred mode of producing antizyme-linker dual protein is by introducing into the subject cells a genetic material which is able to express the fusion protein within cells directly using gene therapy methodology.

Once the dual-function protein is delivered or synthesized in the cells, it is bound rapidly with high affinity and high specificity to the target protein which it degrades.

During the treatment, the level of the target protein is closely monitored by biochemical methods known in the art.

The termination of the degradation process, particularly when the in vivo gene therapy is used, is conveniently regulated by the introduction of linker target protein binding inhibitors.

Generally, inhibitors of proteolysis which can be added include: 1) inhibitors which are not based on amino acids, such as p-aminobenzamidine, FK-448 and camostat mesilate; 2) amino acids and modified amino acids, such acid derivatives; 3) peptides and modified peptides, e.g., bacitracin, antipain, chymostatin and amastatin; and 4) polypeptide protease inhibitors, e.g., aprotinin, Bowman-Birk inhibitor and soybean trypsin inhibitor. Furthermore, complexing agents and some mucoadhesive polymers also display enzyme inhibitor activity.

1. In Vivo Method For Targeted Degradation of Protein

In the in vivo approach, antizyme cDNA, linker cDNA and the expression vectors are prepared as described in Example 1. Then the linker, which is previously identified, tested for its affinity and specificity for the target protein is fused to the antizyme according to Example 2. The plasmid encoding the antizyme-linker fusion protein is prepared and used to transfect subject's cells, according to procedures described in Example 11. In the cells, the plasmid is transcribed into mRNA and the fusion dual-function protein is expressed. Since the linker is a target protein specific, it binds with high affinity to the target protein and degrades it according to the invention.

In vivo, thus, the genetic material encoding the dual-function protein is transferred directly into the subject's cells or tissue. This option is particularly useful for degradation of target proteins in tissues or cells where individual cells cannot be cultured in vitro or where the cultured cells cannot be re-implanted. To ensure the efficiency of the method and expression of the dual-fusion protein at suitably high levels, the coding DNA sequence is engineered to be flanked by an appropriate regulatory sequence such as a viral promoter for ensuring high level expression.

The transfer of genetic material according to the invention is designed to insert genes into cells as extrachromosomal elements not to be integrated into chromosomes. The method is intended to be regulatory in an on-off system rather than permanent genetic modification and stable long-term expression used for true gene therapy.

The method for transfer of genetic material in vivo utilizes, for example, adenovirus vectors, herpes simplex vectors, receptor mediated endocytosis and liposomes, among others, as well as nonviral systems or replication incompetent viruses. Genetic material transfer is achieved, for example, by direct injection, electroporation, particle bombardment, receptor-mediated endocytosis or using liposomes targeted for specific cells or tissues.

2. Ex Vivo Method For Targeted Degradation of Proteins

In the ex vivo approach, the genetic material, that is antizyme cDNA and linker cDNA, are built into the expression vector, for example plasmid, cloned and transferred into cells, preferably subject's cells, grown in culture, that is grown in vitro and extracorporally. These cells are then transformed and expanded by cell culture in vitro and only then introduced into the subject. To avoid immune system rejection the autologous cells are normally used. For this purpose, the cells are collected initially from the subject to be treated, grown in culture, transformed and reintroduced by implantation into the same subject.

The ex vivo transfer of genetic material is achieved by and utilizes, for example, retrovirus vectors, adeno-associated virus vectors, and to a lesser degree, adenovirus vectors, herpes simplex vectors and liposomes.

The ex vivo transfer of genetic material involves essentially four steps:

(a) cloning a dual-function genetic material into a vector, such as retroviral vector;

(b) transfecting the subject's cells where the targeted protein degradation is to occur with the genetic material encoding recombinant dual-function protein;

(c) verifying the expression of the dual-function protein in the cells; and (d) reimplanting these cells in the patient.

The methods used for in vivo gene therapy applicable to the targeted degradation of proteins according to the invention are known in the art and are described, for example, in *Molecular Biotechnology: Therapeutic Applications and Strategies,* Sunil Maulik, Solil D. Patel, WILEY-LISS, A JOHN WILEY & SONS, Inc., New York, (1997); *Medical Genetics*, pp. 252–257, George H. Sack, McGraw-Hill, New York (1999); *Human Molecular Genetics,* 551–588, T. Strachan, A. P. Read, Bios Scientific Publishers, WILEY-LISS, A JOHN WILEY & SONS, Inc., New York (1998); and *Clinical Trials of Genetic Therapy with Antisense DNA and DNA Vectors,* Ed. Enc Wickstrom, Marcell Decker, Inc., New York (1998), all the above hereby incorporated by reference.

The above outlined general methods are used for specific destruction of target proteins intracellularly.

3. In Vitro or Ex Vivo Production of the Dual-Function Protein

Using either in vitro or ex vivo methods described above and in examples, the dual-function antizyme-linker fusion protein is prepared and delivered in the conventional way using pharmaceutically acceptable delivery vehicles and routes. This type of delivery needs to assure that the protein is properly protected from the destruction by digestive proteases when administered orally, or destroyed in the body before it reaches the target cells or tissue.

In this mode, the dual-function protein may be delivered orally, intravenously, intramuscularly, intraperitoneally, subcutaneously as aerosol, or using any other mode of delivery known in the art.

B. Modes of Delivery and Administration

In order to avoid the major drawbacks of delivery of proteins, such as instability in the proteolytic environment of the GI tract and poor absorbability through the mucosa, fusion protein containing compositions are preferably prepared as sterile solutions and administered to patients by daily injection. In this particular instance, the dual-function protein is prepared ex vivo, isolated, purified and administered to a mammalian subject. However, this form of drug delivery could cause pain and inconvenience to patients and thus could be poorly accepted. Many novel delivery systems have been developed to address these problems (*Trends Biotech;,* 16(8): 343–9, (1998), *J. Pharmaceut. Sci,* 87(11): 1331:1334, (1998)). Examples include, but are not limited to combinations of:

1. Targeted delivery to cells or tissues to be treated or orally nasally, as injectable, etc., as alternate sites of delivery to a site where the target protein appears.
2. Formulations containing the dual-function protein for sustained release.
3. Formulations for administration of concentrated dual-function protein into cells at the mucosal surface.
4. Formulations modified for enhanced absorption into cells.
5. Formulation for inhibition of proteolysis including protease inhibitors, chemical modification of the peptide molecule to produce prodrugs and analogs (*Nippon Rinsho. Jap. J. Clin. Med.,* 56(3): 601–7 (1998) and genetic engineering of proteolytically resistant forms.

A number of novel delivery systems have been approved by the FDA (*J. Pharmaceut. Sci.,* 87:1331–4 (1998). In many cases, a given formulation incorporates elements of several of the above mentioned approaches. Development and optimization of an oral drug delivery systems tends to be specific for each peptide drug. (*J. Pharmaceut, Sci.,* 85:1282–5 (1996).

Examples of formulations which prevents proteolytic degradation of the dual-function protein, sustained release and enhanced absorption follow.

Proteins may be delivered via microparticles or microsphere Gelatin capsules coated various concentrations of sodium alginate, for example, 20% w/v, and cross-linked with appropriate concentrations of calcium chloride are resistant to the harsh environment of the stomach and deliver the drug to the distal gastrointestinal tract where drug absorption occurs. (*J. Biomaterials Sci., Polymer Ed.,* 7(1): 39–48 (1995). Molecules can also be incorporated into biodegradable microparticles to reduce the effect of gut secretions and to enable the absorption of proteins in an unaltered form. The uptake of microparticulates through the gut wall is accepted as a true biological phenomenon but the mechanism and route of uptake have not been established. Lipid delivery vehicles enhance microparticle uptake and the selective transport of microspheres across M cells (*J. Anatomy,* 189 (Pt3): 487–90 (1996). Microparticles and microspheres also allow sustained release. Gelatin nanoparticle-poly(lactic-co-glycolic acid) (PLGA) microsphere composites can be prepared by encapsulating protein-loaded gelatin nanoparticles in PLGA microspheres. This encapsulation is conducted by using a phase separation method and a solvent extraction method. Protein release experiments indicate that this composite system possesses sustained release characteristics. This system also demonstrates the capability of preventing the denaturation of protein (*J. Pharmaceut. Sci.,* 86(8): 891–5 (1997).

Poly(vinyl alcohol) (PVA) hydrogel nanoparticles have been prepared by using a water-in-oil emulsion technology plus cyclic freezing-thawing process. The PVA hydrogel nanoparticles prepared by this method are suitable for protein/peptide drug delivery since formation of the hydrogel does not require crosslinking agents or other adjuvants and does not involve any residual monomer. The PVA hydrogel nanoparticles swell in an aqueous solution and the swelling degree increases with the increase of temperature. In vitro release studies show that bovine serum albumen (BSA) release from the nanoparticles can be prolonged to 30 h. The BSA release follows a diffusion-controlled mechanism. The number of freezing-thawing cycle and release temperature both influence BSA release rate considerably. Less freezing-thawing cycle or higher release temperature leads to faster drug release. The BSA is stable during preparation of the PVA hydrogel nanoparticles (*J. Controlled Release,* 56(1–3): 117–26 (1998).

Another route of delivery for proteins are mucoadhesives. Mucoadhesives are polymeric delivery systems for use to concentrate protein and peptide pharmaceuticals at the mucosal surface. The first generation of bioadhesive drug delivery systems were based on natural or synthetic macromolecules, often already well accepted and used as pharmaceutical excipients for other purposes, which show the ability to adhere to humid or wet mucosal tissue surfaces. These novel dosage forms were mainly expected to allow for a possible prolongation, better localization and/or intensified contact to mucosal tissue surfaces. Some of the mucoadhesive polymers were found to display other important biological activities, i.e., inhibition of proteolytic enzymes and or modulation of the permeability of usually tight epithelial tissue barriers. Rather than being just adhesives, mucoadhesive polymers may therefore be considered as a novel class of multi functional macromolecules with a number of desirable properties for their use as biologically active drug delivery adjuvants which are particularly useful in the context of peptide and protein drug delivery. Carbopol (polyacrylic) polymers with strong bioadhesive properties also can inhibit lumenal degradation of peptide or proteins, offering multiple advantages for their uses in oral drug delivery (*J. Pharm. Pharmacol.,* 48(1): 17–21, (1996), *Pharmaceut. Res,* 12(9): 1293–8 (1995). The mucoadhesive polymers carbomer 934P and chitosan hydrochloride are able to enhance the intestinal absorption of some agents such as buserelin in vivo, and are therefore suitable excipients in peroral delivery systems for peptide drugs 13(11): 1668–72 (1996).

Mucoadhesives include monolithic type devices in which the drug is dispersed throughout the polymer and protein-polymer conjugates where the drug is covalently bound to the polymer. Advanced delivery systems include systems containing mucoadhesive polymers providing an intimate contact to the mucosa, thereby reducing the drug degradation between delivery system and absorbing membrane. They also may contain controlled release systems which provide a simultaneous release of protein and inhibitor or inhibitor prodrug or the immobilization of enzyme inhibitors on delivery systems (*J. Controlled Release,* 52(1–2):1–16 (1998); *J. Med. Chem,* 41(13): 2339–44 (1998).

C. Administration of Genetic Material

The administration to the subject of the DNA is done by means of a composition comprising the cDNA of the dual-function protein and a pharmaceutically-acceptable carrier and/or other agents such as recombinase enzymes, a lipid agent, a lipid and protein agent, and the like.

Typically, the carrier may comprise solid, liquid or gaseous carriers. Examples of carriers are aqueous solutions, including water, buffered, aqueous solutions and the like.

While it is possible for the cDNA to be administered alone it is preferable to administer it as a pharmaceutical formulation.

In the preferred embodiment of the invention, the DNA of the above composition comprises a DNA sequence encoding the dual-function protein.

The delivery of the cDNA into the cell may be conducted by a variety of techniques discussed above. These encompass providing the DNA enveloped by a lipid layer (liposomes), further complexed with a protein and a lipid or a dendrimer.

The complexing the cDNA encoding the dual-function protein with lipid, lipid-protein, or dendrimer is especially applicable to in vivo transfection since less cell lethality is encountered, the DNA is protected from DNase degradation and the method is compatible with intracorporeal injection or administration.

One concern about the direct intravenous delivery of genetic material in vivo is the ability of the polynucleotide to survive in circulation long enough to arrive at the desired cellular destination.

In this respect, the coating or masking of the DNA is of extreme utility. The utilization of liposomes, a lipoproteic, or a dendrimer coating is extremely useful. In addition, a successful liposome system uses the cationic lipid reagent dioleyloxytrimethalammonium (DOTMA). DOTMA may be mixed with phosphatidyl ethanolamine (PE) to form the reagent Lipofectin®. When this reagent is utilized to carry the polynucleotides the liposomes are mixed with the DNA and readied for administration.

The DNA may be conveniently enveloped by a lipid layer (liposomes), encapsulated by a lipid and a protein layer, or is complexed to dendrimer. The choice of the foregoing preparations will vary depending on the cell type used, the in vitro, ex vivo or in vivo conditions and the inherent limitations of each transfection method. Preferred conditions for enveloping the cDNA with a lipid layer are as follows. The cDNA is admixed with a lipid such as dioleophosphatidyl ethanolamine, dipalmitoylphosphatidylethanolamine (dipalmitoyl PtdEtn), palmitoyloleoylphosphatidylethanolamine (palmitoyloleoyl PtdEtn), dioleoylphosphatidylcholine (PtdCho), dimyristoylphospatidylethanolamine (dimyristoyl PtdEtn), diphytanoylgeycerophosphatidylethanolamine (diphytanoyl PtdEtn), N-monomethyl PtdEtn, and N-dimethyl PtdEtn in a proportion of about 1 $\mu$g: 1 nmole to 1 $\mu$g: 500 nmoles, in an aqueous solution. Other components and proportions are permissible when this technology is applied to the in vivo method. The pH of the solution may be adjusted to about 8 to 10, and more preferably about 9. In addition to the above, ingredients such as a buffer and other known components may also be added to this composition. The amounts in which these components may be added are standard in the art and need not be further described herein.

In addition to the above, efficient transfer of genetic material requires the targeting of the genetic material encoding the dual function protein to the cell of choice. This can be attained by procedures based upon receptor mediated endocytosis according to *J. Biol. Chem.*, 262:4429(1987); *J. Biol.Chem.*, 263:14,621 (1988)). This technology utilizes a cell-specific ligand-polylysine complex bound to the DNA polynucleotide sequence through charge interactions. This complex is taken up by the target cells. The successful transfection of a similar hepatoma cell line resulting in stable expression of enzymatic activity was reported following directed targeting *Biochem. Pharmacol.*, 40:253 (1985)). *PNAS*, (U.S.A.), 87:3410 (1990) and *PNAS*, (U.S.A.) 88:4255 (1991) utilized a transferrin-polycation to attain the delivery of a plasmid into a human leukemic cell line and observed expression of the encoded luciferase gene. These proteins require attachment to the polynucleotide via, for example, a polylysine linker.

Moreover, in many receptor-mediated systems as chloroquine or other disrupters of intracellular trafficking may be required for high levels of transfection. Adenovirus, for instance, has been used to enhance the delivery of polynucleotides in receptor-mediated systems (*PNAS* (U.S.A.), 88:8850 (1991)).

Alternatively, the genetic material may be masked through association with lipids. In one embodiment, the DNA is encased in standard liposomes as described, for example, in U.S. Pat. No. 4,394,448, the relevant portion of the specification of which is hereby incorporated by reference. In another embodiment, the DNA is incubated with a synthetic cationic lipid similar to those described in U.S. Pat. No. 4,897,355. The above-described synthetic cationic lipid effectively mask the DNA when associated therewith. The methods described in the above and below references are hereby incorporated by reference.

The cell recognition element is a molecule capable of recognizing a component on the surface of a targeted cell, covalently linked with a DNA-associating moiety by conventional methods. Cell recognition components include antibodies to cell surface antigens, ligands for cell surface receptors including those involved in receptor-mediated endocytosis, peptide hormones, etc.

Specific ligands contemplated by this invention include carbohydrate ligands such as galactose, mannose, mannosyl 5-phosphate, fucose, sialic groups, N-acetylglucosamine or combinations of these groups as complex carbohydrates such as those found on glycolipids of the blood groups or on various secreted proteins. Other ligands include folate, biotin, various peptides that can interact with cell surface or intracellular receptors such as the chemoattractants peptide containing N-formyl peptides that contain a cystine residue or that interact with cell surface protein such as the human immunodeficiency virus GP-120, and peptides that interact with CD-4. Other ligands include antibodies or antibody fragments. The specificity of the antibodies can be directed against a variety of epitopes that can be expressed on cell surfaces including histocompatibility macromolecules, autoimmune antigens, viral, parasitic or bacterial proteins. Other protein ligands include hormones such as growth hormone and insulin or protein growth factors such as GM-CSF, G-CSF, erythropoietin, epidermal growth factor, basic and acidic fibroblast growth factor and the like. Other protein ligands would include various cytokines that work through cell surface receptors such as interleukin 2, interleukin 1, tumor necrosis factor and suitable peptide fragments from such macromolecules.

The membrane-permeabilizing element of this system is a molecule that aids in the passage of a polynucleotide across a membrane. The liposomes, synthetic cationic lipids, lipid-proteins, and dendrimer described above as DNA-masking components also may function as membrane-permeabilization components.

Additional membrane-permeabilizing components that will facilitate this invention also include polycations that neutralize the large negative charge on polynucleotides. Polycations of this invention include polylysine, polyarginine, poly (lysine-arginine) and similar polypeptides, and the polyamines and the polycationic dendrimers.

The membrane-permeabilizing component that facilitates this invention may be an amphipathic cationic peptide. Amphipathic cationic peptides are peptides whose native configuration is such that the peptide is considered to have a cationic face and a neutral, hydrophobic face. In a preferred embodiment, the peptide is a cyclic peptide. Examples of the amphipathic cationic cyclic peptides of this invention are gramicidin S, and tyrocidines. The peptide may also contain some or all of the amino acids in the D configuration as opposed to the naturally occurring L configuration.

The membrane permeabilizing elements, i.e., the cyclic peptide and optional phospholipid and polyamine, may be added to the composition simultaneously or consecutively. Preferably, the cyclic peptide is added first, and the phospholipid or polyamine is added later. The molar ratio of added cyclic peptide to added polyamine is preferably from about 1:1 to about 1:3. The molar ratio of added cyclic peptide to added phospholipid is preferably from about 1:1 to about 1:20.

The subcellular-localization element of this system is a molecule capable of recognizing a subcellular component in a targeted cell, covalently linked with a DNA-associating moiety by conventional methods. Particular subcellular components include the nucleus, ribosomes, mitochondria, and chloroplasts. In a preferred embodiment of this invention, the subcellular-localization component is a nuclear-localization component.

The nuclear-localization components include known peptides of defined amino acid sequences, and longer sequences containing these peptides.

In another embodiment, the DNA-associating moiety is a nonspecific DNA binder such as a polycation. Polycations include polylysine, polyarginine, poly(lysine-arginine) and similar polypeptides, and the polyamines and the polycationic dendrimers.

V. Therapeutic Utility

The targeted degradation of selected proteins according to the invention has a wide therapeutic utility. The method is useful for degradation of protein intracellularly but can also be used for destruction of circulating proteins, for example, for destruction of viral proteins, bacterial proteins, parasites, etc. It is also useful for degradation of environmental antigen causing allergies, for degradation antibodies against the antigen. The greatest advantage of the method is its on-off mode whereby using the appropriate activator, for example, polyamines, and appropriate inhibitors, the method of the invention is easily controllable and the whole process is easily regulated.

While the whole scale of diseases are treatable using the method of the invention, the cancer treatment and protection of the normal cells from toxicity cause by the cancer therapy are described here as examples of the invention utility. Other disease typically caused by the excess production of intracellular or extracellular proteins or by protein expressed by mutated genes are advantageously treated in the same way.

A. Treatment of Cancer

Human cancer is commonly caused or exacerbated by the presence of proteins in abnormal form or in excess amount within the cells. Examples of these proteins are products of the oncogenes ras, myc, fos or p53, that disrupt signals limiting normal growth. For destruction of these proteins, a fusion protein is made consisting of antizyme linked to a ligand that binds to these cancer-producing proteins. As described above, the fusion protein cDNA is delivered into the tumor using any of the delivery means described above, where it is translated and expressed in cancer cells. The fusion protein then destroys the oncogene proteins. In this way, normal control of cell growth is restored.

Cancer cells themselves commonly produce polyamines in excess amounts compared to normal cells and would thus seem to produce favorable conditions for expression and production of antizyme and antizyme containing fusion protein. By using a gene requiring polyamine-dependent frameshifting for expression of the encoded fusion protein according to the invention, cancer cells are subject to a more significant degree of inhibition of growth than normal cells, even if both kinds of cells contain the gene encoding the fusion protein, because endogenous polyamines in the cancer cells cause polyamine-dependent frameshifting, as discussed above.

B. Specific Protection of Normal Growing Cells From Toxicity Caused By Cancer Therapy The method of the invention would additionally be useful for protection of normal cells from toxicity caused by cancer therapy.

Commonly used forms of cancer therapy attack growing cells, regardless of whether these are cancer cells or innocent-bystander normal cells. The resultant damage or destruction of normal cells can limit the extent of existing therapeutic treatment that is tolerable.

Cellular proteins that control cell growth include the cyclins, cyclin-dependent kinases with which these cyclins interact and additional proteins that effect the activity or stability of the cyclin-kinase pairs. A fusion protein prepared according to the invention consisting of antizyme linked to a targeting peptide that binds to one of these proteins and causes the fusion protein to be expressed in normal cells, impedes cell growth, thereby protecting the normal cells from the toxicity associated with therapy. Because growth of normal cells must be allowed to remain unimpeded between periodic applications of cancer therapeutic agents, expression of the fusion protein consisting of antizyme linked to a targeting peptide must be limited to the time of treatment. By using a gene requiring polyamine-dependent frameshifting for expression of the encoded fusion protein, it is possible to impede cell growth in normal cells at the desired time by administration of polyamines.

C. Transgenic Plants and Animals

Using the method of the invention, transgenic plants or animals are created in which a gene expressed in one or more tissues encodes a fusion protein, as above, that is expressed as a protein only when polyamines are administered to induce polyamine-dependent frameshifting. By using antizyme fusion proteins that cause the destruction of hormones or the destruction of proteins that either induce or limit the production of hormones in this manner, commercially useful physiologic alterations of the transgenic plants or animals are made to happen at desired times. These include, for example, the ability to alter nutritional content, cause or retard fruit ripening, cause or retard seed germination, and, to facilitate harvesting, cause abscission.

EXAMPLE 1

Antizyme cDNA and Expression Vectors

This example describes methods used for production of antizyme (AZ) cDNA and the expression vectors used.

The rat antizyme λ gt11 partial cDNA clone Z1 was prepared according to *J. Biochem.*, 108: 365–371 (1990) and *Gene*, 113: 191–197 (1992). The dexamethasone-inducible vector pMaMneoZ1 was obtained according to *J. Biol. Chem.*, 167: 13138–13141 (1992). Z1 and pMAMneoZ1 have a 212-amino-acid open reading frame. A numbering convention that specifies the start of this reading frame to be amino acid 1 of antizyme was used.

EXAMPLE 2

Preparation of Antizyme Fusion Proteins and Construction of Plasmids Encoding Antizyme GST Fusions This example describes methods used for preparation of antizyme fusion proteins and for construction of plasmids encoding antizyme glutathione S-transferase (GST) fusions.

Rat AZcDNA Z1 of Example 1 was expressed as a fusion protein C-terminal to glutathione S-transferase (GST) by cloning into the BamHI-EcoRI sites of the pGEX-3 vector according to *Gene*, 67: 31–40 (1988). Deletions within the AZ Z1 212-amino-acid open reading frame were made by PCR, using oligonucleotides that included BamHI or EcoRI sites.

The resulting amplified PCR fragments were restricted and ligated into the pGEX-3 vector to create fusion proteins with various deletions in the antizyme portion. To express the fusion proteins, *Escherichia coli* carrying these recombinant plasmids was induced with isopropylthiogalactopyranoside, (IPTG), and the proteins were then purified with glutathione-Sepharose 4B beads (Pharmacia). For use in the degradation assay, proteins were eluted from beads with 0.1 M glycine and 0.1 M NaCl (pH 2.5), and the eluates were neutralized with 1.5 M Tris-HCl (pH 8.8).

EXAMPLE 3

In Vitro Transcription of cDNA Into cRNA and Translation of cRNA Into a Protein This example describes methods used to achieve in vitro transcription of antizyme cDNA into cRNA and subsequent translation into an appropriate protein.

Plasmid DNA was used as a template to amplify chimeric ODC cDNA or AZ cDNA by PCR, using as the 5' oligonucleotide a primer containing a T7 RNA polymerase recognition site, and the amplified DNA was then transcribed into cRNA with T7 RNA polymerase according to *Mol. Cell. Biol.*, 12: 3556–3562 (1992). cRNA was translated in vitro by using a rabbit reticulocyte lysate (Promega). The mouse ODC, radiolabeled with [$^{35}$S]methionine, was used for a binding assay or, in unlabeled form, for an inhibition assay.

EXAMPLE 4

Antizyme Binding and Inhibitory Activity

This example describes assays used for determination of antizyme binding and inhibitory activity.

Ten microliters of translation lysate containing [$^{35}$S] methionine-labeled mouse ODC was added to 50 µl of phosphate-buffered saline containing 0.05% Triton X-100 and 15 µl of glutathione-Sepharose 4B beads (Pharmacia) bearing the fusion proteins. After shaking at 4° C. for 1 hour, the beads were washed three times with phosphate-buffered saline. The proteins associated with the beads were made soluble in sodium dodecyl sulfate (SDS) sample buffer, and the radiolabeled ODC was analyzed by SDS-polyacrylamide gel electrophoresis (PAGE) and autoradiography.

For the inhibition assay, 10 µl of beads bearing the fusion proteins was mixed with 10 µl of in vitro-translated mouse ODC and incubated on ice for 5 min. ODC activity of the mixture was then determined as described in *Mol. Cell, Biol.*, 12: 3556: 3562 (1992).

EXAMPLE 5

In Vivo Regulation By Antizyme 106–212

This example illustrates assays used to determine in vivo regulation using antizyme 106–212.

DNA encoding antizyme amino acids 106 to 212 (AZ 106–212) was amplified by PCR, using the rat AZ λ gt11 cDNA clone Z1 as the template. An NheI restriction site and start codon ATG were incorporated into the 5' oligonucleotide primer, and a SalI site was incorporated into the 3' primer. The PCR fragment so generated was then cloned into the NheI and SalI sites of the dexamethasone-inducible expression vector pMAMneoZ1 to generate pMAMneoAZ106–212.

Plasmid pMAMneoAZ106–212 is identical to pMAMncoZ1 except that it encodes a truncated form of AZ composed of amino acids 106 to 212 in place of amino acids 1 to 212. Transformants were selected with G418. Pools of stably transformed clones were plated (approximately $10^6$ cells per 100-mm-diameter Falcon dish) and incubated at 37° C. for 16 hours. Dexamethasone was added to the cell culture to a final concentration of 1 µM to induce AZ or AZ 106–212 protein. Cell lysates were prepared after the indicated time of treatment and assayed for ODC activity as described in *Mol. Cell. Biol.*, 12: 3556: 3562 (1992).

EXAMPLE 6

Immunoprecipitation of $^{35}$S-Labeled Ornithine Decarboxylase

This example illustrates method used for immunoprecipitation of $^{35}$S-labeled ornithine.

For immunoprecipitation of $^{35}$S-labeled ornithine, AZ or AZ 106–212 stably transfected HTC cells were plated at a density of about $10^6$ cells per 10-mm-diameter dish (Falcon) and grown overnight. The cells were treated with 1 mM dexamethasone or were left untreated for 4 h and then labeled with [$^{35}$S]methionine for 30 min. Cells were collected in Nonidet P-40 lysis buffer (150 mM NaCl, 1% Nonidet P-40, 50 mM Tris [pH 8.0]). Cell lysates containing $5 \times 10^6$ acid-precipitable cpm were immuno-precipitated with anti-mouse ODC-specific polyclonal rabbit antiserum. Immunoreactive protein was collected by using Pansorbin and subjected to SDS-PAGE and autoradiography.

EXAMPLE 7

Recombinant DNA Constructs

This example describes procedure used for preparation of recombinant DNA constructs used for the expression of fusion proteins by in vitro transcription and translation.

Amplification

The DNA sequence encoding each constituent protein fragment to be expressed was copied by PCR using oligonucleotides that incorporated a common restriction endonuclease recognition site at the point of fusion. The PCR fragments encoding the protein regions to be fused were digested with the common restriction enzyme, ligated, and reamplified using the distal 5' and 3' oligonucleotides. The 5' oligonucleotide used to copy the N-terminal element of each fusion contained a T7 RNA polymerase recognition site placed upstream of the translation initiation AUG codon. The resultant PCR product after the second round of amplification thus contained at the 5' end a T7 RNA polymerase recognition site, followed by an open reading frame encoding the fusion protein.

Plasmids encoding sea urchin cyclin B were provided by Andrey W. Murray (Univ. of Calif., San Francisco).

Antizyme λ gt11

The rat antizyme λ gt11 partial cDNA clone Z1 was obtained from S. Hayashi (Jekei Univ., Tokyo). Z1 has a 212 amino acid open reading frame. A numbering convention that specifies the start of this reading frame to be amino acid 1 of antizyme was used.

The sources and sequences of mouse ODC (M-ODC) and *Trypanosoma brucei* ODC (Tb-ODC) were as described in *Mol. Cell. Biol.*, 14:897–92 (1994).

Fusion NAZ to Proteins

To fuse the 1–97 N-terminal amino acids of antizyme (NAZ) to various proteins, Z1 DNA was amplified by PCR using a 3' oligonucleotide with a HindIII site. Similarly, using PCR, a HindIII site was introduced at the 5' ends of M-ODC, TbODC, Tb376M, Tb422M, and cyclin B amino acids 13–90. PCR amplified fragments were digested or partially digested with HindIII and ligated to make NAZ-M-ODC, NAZ-Tb-ODC, NAZ-Tb376M, NAZ-Tb422M, and NAZ-cyclin B 13–90. To make the C-terminal deletion NAZ-cyclin B 13–90, sequence changes were incorporated into the 3' oligonucleotides which created translation stop codons immediately after cyclin B amino acid 59. CAZ-MODC was made using a similar strategy by ligating antizyme cDNA encoding amino acids 106–212 and mouse ODC cDNA with a Hind III linker. To make fusion proteins of TbODC coupled to the degradation domain of p53, DNA was also amplified by PCR using oligonucleotides that contained a BamHI sites at the TbODC 3' end and at the 5' end of p53 degradation domain (amino acids 100–150). Tb376M, Tb422M and M314T were as described in *Mol. Cell Biol.*, 12: 3556–3562 (1992).

EXAMPLE 8

Degradation Assay

This example describes assay used for protein degradation studies.

Recombinant DNA constructs produced by PCR in Example 6 were used as templates for in vitro transcription by T7 RNA polymerase. RNA was translated in vitro using a rabbit reticulocyte lysate (Promega) in the presence of [$^{35}$S]-methionine. The translated proteins were subjected to degradation in a rabbit reticulocyte lysate extract as described in *Mol. Cell. Biol.*, 13: 2377–2383 (1993).

Degradation was carried out at 30° C. and the labeled protein remaining undestroyed was examined by SDS-PAGE and autoradiography. For densitometric analysis of autoradiograms, images were captured and digitized with a Lighttools Research gel documentation system and quantitated with PPLab Gel version 1.5c software.

To inhibit degradation, incubation was carried out for 2 hours as above, except that 2 mM ATP-S was used in place of ATP and the ATP regenerating system. To test whether the high molecular conjugate of p53 accumulated by ATP-S is the poly-ubiquitinated form of substrate protein, p53 and its conjugate were immuno-precipitated with PAb42I (Ongogene Science) and immuno-blotted with ubiquitin antibodies (Sigma).

EXAMPLE 9

Complexing of Antizyme With the 26S Proteasome

This example describes procedures used for study of ability of antizyme, ornithine decarboxylase or their associated complex to form a complex with the 26S proteasome.

Mouse ODC, GST, GST-AZ or GST-ODC was transcribed and translated in vitro in the presence of [$^{35}$S]-methionine. The in vitro translated GST or GST fusion proteins were directly purified with Glutathione-Sepharose 4B. To isolate a complex of ODC/AZ, ODC was in vitro translated in the presence of $^{35}$S-methionine and GST-AZ fusion proteins were expressed in *E. coli*. These fusion proteins include antizyme amino acids 55–212 (G-AZ-55–212) or antizyme amino acids 106–212 (G-AZ 106–212). These proteins were coupled to glutathione-Sepharose 4B and mixed with the $^{35}$S-labeled in vitro translated ODC. The ODC/AZ complexes were eluted from the beads with 20 mM glutathione and mixed with the 26S protease, the 20S proteasome or the 11S activator, prepared from rabbit reticulocyte lysate as described in Example 7. The mixtures were then loaded on non-denaturing gel for electrophoretic separation, the 26S protease and the 20S proteasome were identified by the fluorogenic peptide overlay assay according to *J. Biol. Chem.*, 267: 22362–22368 (1992) and Coommassie blue staining. The association of ODC/AZ complex with the 26S protease was determined by autoradiography.

EXAMPLE 10

In Vitro Transcription and Translation

This example describes in vitro transcription and translation procedures used for study of fusion proteins.

Recombinant DNAs used for expression of fusion proteins by in vitro transcription and translation were made as follows. The DNA encoding each constituent protein fragment to be expressed was copied by PCR, using oligonucleotides that incorporated a common restriction endonuclease recognition site at the point of fusion. The PCR fragments encoding the protein regions to be fused were digested with the common restriction enzyme, ligated, and reamplified using the distal 5'- and 3'-oligonucleotides. The 5'-oligonucleotide used to copy the N-terminal element of each fusion contained a T7 RNA polymerase recognition site placed upstream of the translation initiation AUG codon. The resultant PCR product after the second round of amplification thus contained at the 5'-end a T7 RNA polymerase recognition site, followed by an open reading frame encoding the fusion protein.

EXAMPLE 11

Transfection and In Vivo Degradation Assay

This example describes transfection and in vivo procedures used for study of in vivo NAZ-induced degradation of fusion proteins.

Constructs TbODC-p53 100–150 and M314T-p53 100–150 were cloned into a mammalian expression vector under the control of the SV40 early promoter according to *Genes and Dev.*, 4:764–778 (1990). The plasmids, along with pMC1 conferring neomycin/G418 resistance were prepared according to *Cell*, 51:503–512 (1987), were used to transfect mutant Chinese hamster ovary C55.7 cells devoid of endogenous ODC activity according to *J. Biol. Chem.*, 257:4603–4509 (1982). Transformants were obtained by subjecting the cells simultaneously to two forms of selection: 1) with the drug G418, selective for cells expressing the neo gene encoded by pMC1, and 2) by incubation in polyamine-deficient medium, selective in the mutant ODC-deficient cells for expression of the transfected ODC gene, which is needed for polyamine biosynthesis. Pools of stably transformed clones were plated (approximately $10^6$ cells/ 100-mm Falcon dish) and incubated at 37° C. for 16 hours. To elicit polyamine-mediated regulation and induce endogenous antizyme, putrescine was added to the culture medium to a final concentration of 100 um. ODC stability was assessed in some experiments by inhibiting protein synthesis with cycloheximide, 100 mg/ml of cell culture medium, and determining the rate of decay of enzymatic activity. Cell lysates were prepared after the indicated time of treatment and assayed for ODC activity as described in *Mol.Cell Biol,* 13:2377–2388 (1993).

EXAMPLE 12

Rapamycin-Induced Dimerization and Degradation

This example describes rapamycin induced dimerization and protein degradation of NAZ-FKBP.

The constructs comprising NAZ and FKBP12 are made and their rapamycin-induced dimerization and degradation tested. The first construct consists of a fusion of NAZ (residus 1–112 of antizyme) and a three-fold reiteration of FKBP12 serving as a specific linker binding with a hemagglutinin (HA) epitope tag. The reporter gene used in the second construct is the EGFP, an enhanced version of the green fluorescent protein (Clontech). EFGP has a Flag epitope tab and the FRB domain of FRAP (three copies) fused to its amino terminus by a (ser-gly-gly)$_3$ spacer, and the last 39 residues of ODC fused to its carboxyl terminus. These two constructs are designated NAZ-FKBP-HA and Flag-FRB-EGFP-CODC.

After in vitro transcription-translation of these fusion proteins, their association with each other, upon addition of rapamycin, is detected by immunoprecipitation with anti-HA, followed by Western blotting using anti-flag antibodies. The degradation of FRB-EGFP-CODC by the 26S proteasome is followed using a fluorescence spectrophotometer. EGFP has fluorescent activity when made in a cell-free translation system (*Current Biology,* 7:R207-R208 (1997)). Determination is made whether degradation is dependent on the presence of both NAZ-FKBP-HA and rapamycin. Inhibitors specific for proteasomes, e.g., lactacystin, present such degradation. When a decrease of the EFGP half life is observed, the system is further tested in cultured cells. The two constructions are cloned in the pBJ5 mammalian expression vector and both transiently transfected into CHO cells. As a control, FRB-EGFP-CODC is transfected without NAZ-FKBP-HA. In the in vitro experiment, co-immunoprecipitation is used to test for rapamycin-dependent formation of heterodimers. The fluorescence intensity in the cells, after addition of rapamycin, is examined under a fluorescence microscope and in parallel by FACS. The half life of EGFP is determined after treatment of the cells with rapamycin and cycloheximide, the latter to prevent de novo protein synthesis.

EXAMPLE 13

A Method For Specific Protection of Normal Growing Cells Form Toxicity Caused By Cancer Therapy This example illustrates a method for specific protection of normal growing cells from toxicity caused by cancer therapy.

Commonly used forms of cancer therapy attack growing cells, regardless of whether these are cancer cells or innocent-bystander normal cells. The resultant damage or destruction of normal cells can limit the extent of existing therapeutic treatment that is tolerable.

Cellular proteins that control cell growth include the cyclins, cyclin-dependent kinases with which these cyclins interact and additional proteins that effect the activity or stability of the cyclin-kinase pairs. A fusion protein prepared according to the invention consisting of antizyme linked to a targeting peptide that binds to one of these proteins and causes the fusion protein to be expressed in normal cells, impedes cell growth, thereby protecting the normal cells from the toxicity associated with therapy. Because growth of normal cells must be allowed to remain unimpeded between periodic applications of cancer therapeutic agents, expression of the fusion protein consisting of antizyme linked to a targeting peptide must be limited to the time of treatment. By using a gene requiring polyamine-dependent frameshifting for expression of the encoded fusion protein, it is possible to impede cell growth in normal cells at the desired time by administration of polyamines. Prior to cancer chemotherapy, patient bone marrow cells is removed by aspiration. The mixture of bone marrow cells is treated to deplete the cell population of cancer cells and to enrich the cell population with stem cells capable of regenerating normal bone marrow using methods known in the art for selective cultivation and fractionation based on physical cell characteristics or cell surface markers.

The resultant population enriched in stem cells is transfected with DNA encoding an NAZ-linker fusion protein designed to block cell growth when synthesis of the NAZ-linker is induced within cells by polyamine-dependent frameshifting.

The DNA is produced within bacteria as a plasmid containing a gene composed of NAZ with polyamine-dependent frameshifting region fused in frame to a linker with high affinity and specificity for a cyclin, for example cyclin B. A linker is designed as described in Section I, C. For cyclin B, a natural interaction partner exists in the form of a cyclin-dependent kinase and it or a portion of it capable of maintaining such interaction constitutes a natural candidate linker.

DNA is transfected into the cell population by chemical or physical means using standard methods. The cell population so transfected is then reinfused into the patient and allowed to populate the bone marrow. A portion of the normal bone marrow stem cell population thus consists of cells the growth of which is prevented or permitted depending on whether polyamines are fed or infused (cell population may not grow) or withheld (cell population may grow).

Prior to and during treatment with agents that selectively kill growing cells, i.e. cancer cells by intention and normal cells as an undesired toxic effect, patient is treated with polyamines to deplete cells expressing the NAZ-linker of cyclin B by inducing destruction of cyclin B. Cells so depleted of cyclin B are incapable of growth and replication and are thus protected from damage or death.

Polyamine treatment is repeated to coincide with each round of cancer therapy. Because multiple rounds of therapy over a protracted period are commonly employed in cancer treatment, the method described is more effective than infusing the stem cell population after therapy is completed, at which time the patient may be suffering from lethal bone marrow failure.

What is claimed is:

1. A method for in vivo intracellular ubiquitin independent degradation of a target protein which can be covalently or non-covalently linked to N-terminal domain of antizyme in cells of a mammal subject in need of such target protein degradation, said method comprising a step of (i) administering to the subject or to the subject's cells the protein consisting of the N-terminal domain portion of antizyme consisting of up to 97 amino acids or the fusion protein consisting of the N-terminal domain portion of antizyme and the linker recognizing the target protein with high specificity and binding the target protein with high affinity;

(ii) inducing expression of the protein or fusion protein of step (i) within the cells; or (iii) administering to the subject polyamines sufficient to induce the formation of the protein of step (i).

2. The method of claim 1 wherein the induction of the protein for degradation of the target protein covalently or non-covalently linked to the N-terminus domain of antizyme in vivo is by providing cells of the mammal subject with a protein consisting of the N-terminal domain portion of antizyme consisting of up to 97 amino acids or with a fusion protein consisting of the N-terminal domain portion of antizyme consisting of up to 97 amino acids and of a linker recognizing the target protein with high specificity and binding the target protein with high affinity, provided that the linker is not C-terminus of antizyme; and (b) inducing the ubiquitin independent degradation of the target protein by covalently or non-covalently linking said protein consisting of the N-terminal domain portion of antizyme with the target protein directly or through the linker.

3. The method of claim 2 wherein upon the binding, the N-terminal domain of the protein of step (i) promotes and directs the target protein degradation.

4. The method of claim 3 wherein the N-terminal domain of the protein of the fusion protein of step (i) comprises amino acids 55–84.

5. The method of claim 4 wherein the protein of step (i) or the linker of the fusion protein of step (i) binds to the target protein non-covalently.

6. The method of claim 5 wherein the protein of step (i) or the linker of the fusion protein of step (i) binds to the target protein covalently.

7. The method of claim 1 wherein the antizyme comprises N-terminal domain consisting of up to 99 amino acids.

8. The method of claim 7 wherein the N-terminal domain of the protein or the fusion protein promotes and directs the target protein degradation.

9. The method of claim 8 wherein the N-terminal domain of the protein of the fusion protein comprises amino acid 55–84.

10. The method of claim 9 wherein the fusion protein or the linker of the fusion protein binds to the target protein non-covalently.

11. The method of claim 9 wherein the fusion protein or the linker of the fusion protein binds to the target protein covalently.

12. A method for selective and targeted degradation of intracellular target proteins by providing to a subject in need of such treatment a protein agent comprising a C-terminal domain and a N-terminal domain (NAZ) consisting of about 97 amino acids of a N-terminus half of antizyme.

13. The method of claim 12 wherein the C-terminal domain acts as a linker between the target protein and the protein agent.

14. The method of claim 13 wherein the linker causes association between the protein agent and the target protein.

15. The method of claim 14 wherein upon such association, N-terminal domain promotes and directs the target protein degradation.

16. The method of claim 15 wherein the protein agent is antizyme.

17. The method of claim 16 wherein the amino acid chain of the N-terminal domain responsible for protein degradation are amino acids 55–84.

* * * * *